US012662533B2

(12) United States Patent (10) Patent No.: US 12,662,533 B2

Mandelin et al. (45) Date of Patent: Jun. 23, 2026

(54) STABLE ANTI-CLEVER-1 ANTIBODY FORMULATION

(71) Applicant: Faron Pharmaceuticals OY, Turku (FI)

(72) Inventors: Jami Mandelin, Helsinki (FI); Marita Vainio, Turku (FI)

(73) Assignee: Faron Pharmaceuticals OY, Turku (FI)

( * ) Notice: Subject to any disclaimer, the term of this patent is extended or adjusted under 35 U.S.C. 154(b) by 815 days.

(21) Appl. No.: 18/001,689

(22) PCT Filed: Jun. 14, 2021

(86) PCT No.: PCT/FI2021/050442

§ 371 (c)(1),
(2) Date: Dec. 13, 2022

(87) PCT Pub. No.: WO2021/255336

PCT Pub. Date: Dec. 23, 2021

(65) Prior Publication Data

US 2023/0235046 A1 Jul. 27, 2023

(30) Foreign Application Priority Data

Jun. 15, 2020 (FI) ...................................... 20205624

(51) Int. Cl.

| | |
|---|---|
| *C07K 16/28* | (2006.01) |
| *A61K 9/08* | (2006.01) |
| *A61K 39/00* | (2006.01) |
| *A61K 47/18* | (2017.01) |
| *A61K 47/26* | (2006.01) |
| *A61P 35/00* | (2006.01) |

(52) U.S. Cl.

CPC ................ *C07K 16/28* (2013.01); *A61K 9/08* (2013.01); *A61K 47/183* (2013.01); *A61K 47/26* (2013.01); *A61P 35/00* (2018.01); *A61K 2039/505* (2013.01)

(58) Field of Classification Search

None
See application file for complete search history.

(56) References Cited

U.S. PATENT DOCUMENTS

| | | |
|---|---|---|
| 2005/0276823 A1 | 12/2005 | Cini et al. |
| 2019/0030180 A1 | 1/2019 | Harlow et al. |
| 2023/0263895 A1 | 8/2023 | Andya et al. |
| 2025/0197520 A1 | 6/2025 | Adler et al. |

FOREIGN PATENT DOCUMENTS

| | | |
|---|---|---|
| CN | 109311983 A | 2/2019 |
| CN | 109496149 A | 3/2019 |
| CN | 110753701 A | 2/2020 |
| CN | 110840830 A | 2/2020 |

| | | |
|---|---|---|
| EP | 2331090 B1 | 1/2018 |
| EP | 2991678 B1 | 4/2020 |
| EP | 3445785 B1 | 6/2022 |
| JP | 2006502116 A | 1/2006 |
| JP | 2016065091 A | 4/2016 |
| JP | 2019519475 A | 7/2019 |
| JP | 2020011962 A | 1/2020 |
| WO | 03057130 A2 | 7/2003 |
| WO | 2008071394 A1 | 6/2008 |
| WO | 2010122217 A1 | 10/2010 |
| WO | 201603153 A1 | 6/2016 |
| WO | 2017121867 A1 | 7/2017 |
| WO | 2017182705 | 10/2017 |
| WO | 2018122053 A1 | 7/2018 |
| WO | 2018154319 A1 | 8/2018 |
| WO | 2018170145 A1 | 9/2018 |

OTHER PUBLICATIONS

Non-Final Office Action issued for Brazilian Patent Application No. 112022022700-0 on Jun. 17, 2025, 5 pages.
Office Action issued in the corresponding Japanese application No. 2022-577231 on May 27, 2025, 10 pages.
Office Action issued in the corresponding Chinese application No. 202180043044.0 on May 16, 2025, 15 pages.
Bono "Immune activation in first-in-human anti-macrophane anti-macrophage antibody (anti-Clever-1 mAb; FP1305) phase I/II MAT-INS tria: Part I dose-esclation, safety, and efficacy results", Journal of Clinical Oncology 38, No. 15_suppl (May 20, 2020), 3 pages.
Wang et al., "Antibody Structure, Instability and Formulation", Journal of Pharmaceutical Sciences, vol. 96, No. 1, Jan. 2007, 27 pages.
Basle et al., "Physicochemical Stability of Monoclonal Antibodies: A review", Journal of Pharmaceutical Sciences 109(2020) 169-190.
"International Nonproprietary Names for Pharmaceutical Substances (INN)", Who Drug information, vol. 34 No. 3, 2020, Recommended INN: List 84, 115 pages.
Kzhyshkowska, "Multifunctional Receptor Stabilin-1 in Homeostasis and Disease", Mini-Review, The Scientific World Journal (2010) 10, 2039-2053.
International Search Report and Written Opinion issued in PCT/FI2021/050442 dated Sep. 28, 2021, 15 pages.

(Continued)

*Primary Examiner* — Ruixiang Li

(74) *Attorney, Agent, or Firm* — ROTHWELL, FIGG, ERNST & MANBECK, P.C.

(57) ABSTRACT

The invention relates to stable formulations comprising an anti-CLEVER-1 antibody or antigen binding fragment(s) thereof, a buffer and a stabilizing agent. The present invention further relates to stable formulations of an anti-CLEVER-1 antibody or antigen binding fragments thereof for use in treatment of various diseases and disorders.

19 Claims, 11 Drawing Sheets

Specification includes a Sequence Listing.

(56) References Cited

OTHER PUBLICATIONS

Chang et al. (2015) "Lyophilized biologics." Lyophilized biologics
and vaccines: modality-based approaches (pp. 93-119).
Office Action for corresponding Canadian Patent Application No.
3,178,066 issued on Mar. 5, 2026, 5 pages.

Heavy chain

```
QVTLKESGPT LVKPTQTLTL TCSFSGFSLS TSGMGIGWIR QPPGKALEWL  50
AHIWWDDDKR YNPALKSRLT ISKDTSKNQV VLTMTNMDPV DTATYYCARH 100
YGYDPYYAMD YWGQGTLVTV SSASTKGPSV FPLAPCSRST SESTAALGCL 150
VKDYFPEPVT VSWNSGALTS GVHTFPAVLQ SSGLYSLSSV VTVPSSSLGT 200
KTYTCNVDHK PSNTKVDKRV ESKYGPPCPP CPAPEFEGGP SVFLFPPKPK 250
DTLMISRTPE VTCVVVDVSQ EDPEVQFNWY VDGVEVHNAK TKPREEQFNS 300
TYRVVSVLTV LHQDWLNGKE YKCKVSNKGL PSSIEKTISK AKGQPREPQV 350
YTLPPSQEEM TKNQVSLTCL VKGFYPSDIA VEWESNGQPE NNYKTTPPVL 400
DSDGSFFLYS RLTVDKSRWQ EGNVFSCSVM HEALHNHYTQ KSLSLSLGK  449
```

Light chain

```
EIVLTQSPGT LSLSPGERAT LSCTASSSVS SSYLHWYQQK PGKAPKLLIY  50
RTSNLASGVP SRFSGSGSGT DYTLTISSLQ PEDFATYYCH QYHRSPPTFG 100
QGTKLEIKRT VAAPSVFIFP PSDEQLKSGT ASVVCLLNNF YPREAKVQWK 150
VDNALQSGNS QESVTEQDSK DSTYSLSSTL TLSKADYEKH KVYACEVTHQ 200
GLSSPVTKSF NRGEC                                       215
```

Fig. 1

| | Concentration by UV 280 (mg/ml) | | | | | | | |
|---|---|---|---|---|---|---|---|---|
| | #2 | | #3 | | #5 | | #8 | |
| | n1 | n2 | n1 | n2 | n1 | n2 | n1 | n2 |
| T0 | 108 | 109 | 105 | 96 | 104 | 105 | 117 | 117 |
| 1 week at 5 ± 3 °C | 108 | 109 | 103 | 100 | 104 | 103 | 119 | 122 |
| 1 week at 35 °C | 112 | 112 | 102 | 102 | 103 | 105 | 125 | 125 |

Fig. 2

| | Turbidity by absorption measurement at 350 nm | | | | | | | |
|---|---|---|---|---|---|---|---|---|
| | #2 | | #3 | | #5 | | #6 | |
| | n1 | n2 | n1 | n2 | n1 | n2 | n1 | n2 |
| T0 | 0.46 | 0.44 | 0.49 | 0.50 | 0.64 | 0.64 | 0.63 | 0.64 |
| 1 week at 5 ± 3 °C | 0.43 | 0.44 | 0.46 | 0.48 | 0.60 | 0.60 | 0.59 | 0.59 |
| 1 week at 35 °C | 0.46 | 0.46 | 0.48 | 0.49 | 0.63 | 0.64 | 0.62 | 0.62 |

| | Turbidity by absorption measurement at 510 nm | | | | | | | |
|---|---|---|---|---|---|---|---|---|
| | #2 | | #3 | | #5 | | #6 | |
| | n1 | n2 | n1 | n2 | n1 | n2 | n1 | n2 |
| T0 | 0.09 | 0.07 | 0.09 | 0.10 | 0.13 | 0.13 | 0.15 | 0.15 |
| 1 week at 5 ± 3 °C | 0.07 | 0.07 | 0.07 | 0.07 | 0.10 | 0.10 | 0.10 | 0.10 |
| 1 week at 35 °C | 0.07 | 0.07 | 0.08 | 0.08 | 0.10 | 0.10 | 0.11 | 0.11 |

Fig. 3

| | Concentration by UV 280 (mg/ml) | | | | | | | | | | | | | | | |
|---|---|---|---|---|---|---|---|---|---|---|---|---|---|---|---|---|
| | #6 | | #6 + PS20 | | #3-1 | | #3-1 +PS20 | | #3-2 | | #3-2 +PS20 | | #3-3 | | #3-3 +PS20 | |
| | n1 | n2 | n1 | n2 | n1 | n2 | n1 | n2 | n1 | n2 | n1 | n2 | n1 | n2 | n1 | n2 |
| T0 | 28 | 29 | 30 | 28 | 27 | 26 | 26 | 27 | 25 | 26 | 26 | 26 | 27 | 28 | 26 | 27 |
| Freeze/Thaw | 28 | 30 | 29 | 30 | 28 | 27 | 25 | 25 | 28 | 25 | 26 | 26 | 27 | 26 | 28 | 27 |
| Light Stress | 29 | 29 | 28 | 29 | 28 | 25 | 26 | 24 | 25 | 25 | 26 | 28 | 29 | 27 | 28 | 27 |
| 1 week at 35 °C + shaking | 30 | 30 | 30 | 30 | 28 | 27 | 27 | 27 | 28 | 29 | 28 | 28 | 27 | 29 | 28 | 27 |
| 2 weeks at 35°C+ shaking | 29 | 30 | 29 | 30 | 26 | 26 | 26 | 26 | 25 | 26 | 25 | 28 | 25 | 26 | 28 | 27 |

| | Concentration by UV 280 (mg/ml) | | | | | |
|---|---|---|---|---|---|---|
| | #3-1 + PS20 + meth | | #3-2 + PS20 + meth | | #3-3 + PS20 + meth | |
| | n1 | n2 | n1 | n2 | n1 | n2 |
| Light stress | 24 | 25 | 25 | 25 | 28 | 26 |

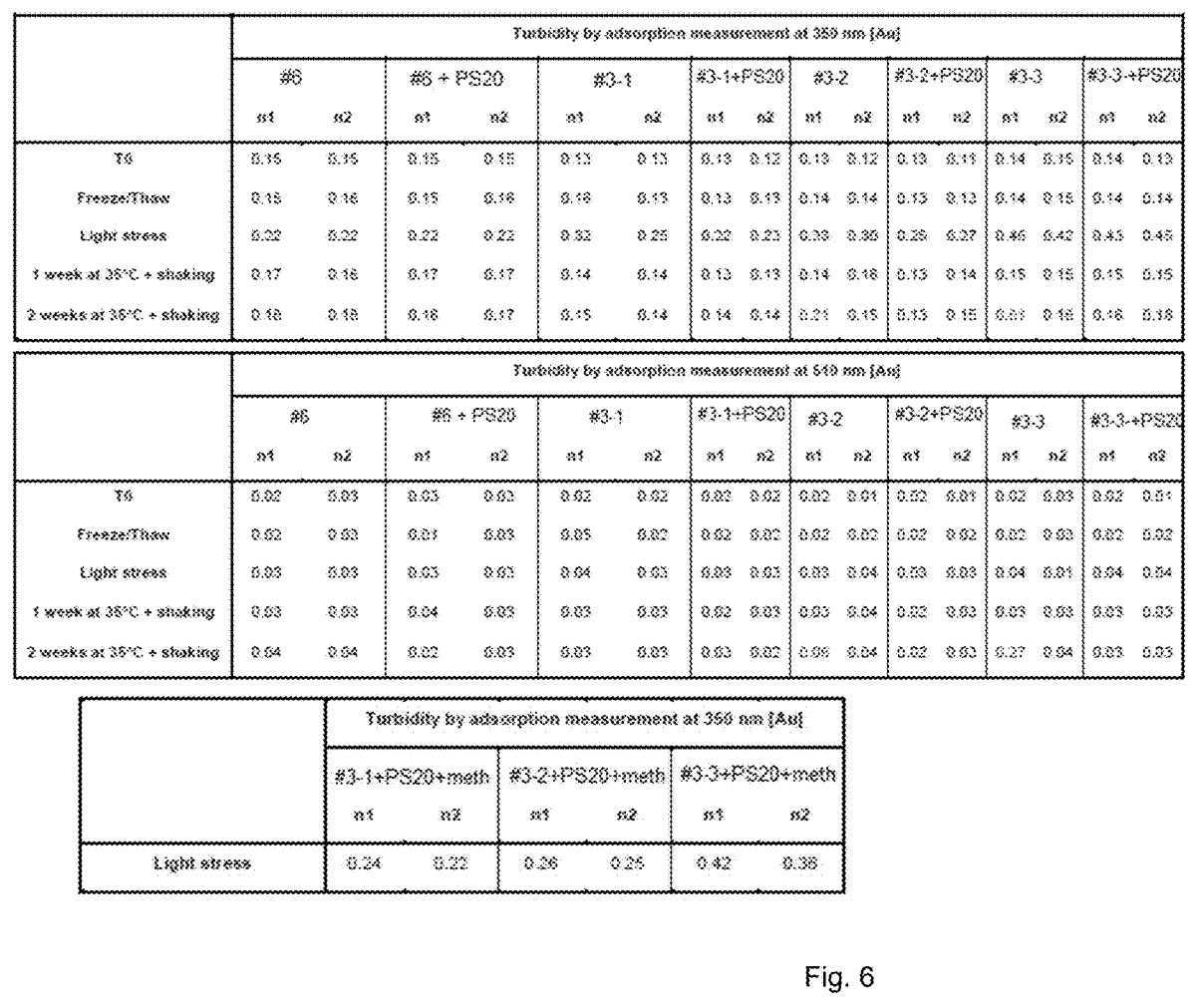

| | Turbidity by adsorption measurement at 350 nm [Au] | | | | | | | | | | | | | | |
|---|---|---|---|---|---|---|---|---|---|---|---|---|---|---|---|---|
| | #6 | | #6 + PS20 | | #3-1 | | #3-1+PS20 | | #3-2 | | #3-2+PS20 | | #3-3 | | #3-3+PS20 | |
| | n1 | n2 | n1 | n2 | n1 | n2 | n1 | n2 | n1 | n2 | n1 | n2 | n1 | n2 | n1 | n2 |
| T0 | 0.15 | 0.15 | 0.15 | 0.15 | 0.13 | 0.13 | 0.13 | 0.12 | 0.13 | 0.12 | 0.13 | 0.11 | 0.14 | 0.15 | 0.14 | 0.13 |
| Freeze/Thaw | 0.15 | 0.16 | 0.15 | 0.16 | 0.16 | 0.13 | 0.13 | 0.13 | 0.14 | 0.14 | 0.13 | 0.13 | 0.14 | 0.15 | 0.14 | 0.14 |
| Light stress | 0.22 | 0.22 | 0.22 | 0.22 | 0.32 | 0.25 | 0.22 | 0.23 | 0.33 | 0.36 | 0.26 | 0.27 | 0.46 | 0.42 | 0.43 | 0.45 |
| 1 week at 35°C + shaking | 0.17 | 0.18 | 0.17 | 0.17 | 0.14 | 0.14 | 0.13 | 0.13 | 0.14 | 0.18 | 0.13 | 0.14 | 0.15 | 0.15 | 0.15 | 0.15 |
| 2 weeks at 35°C + shaking | 0.18 | 0.18 | 0.18 | 0.17 | 0.15 | 0.14 | 0.14 | 0.14 | 0.21 | 0.15 | 0.13 | 0.15 | 0.61 | 0.18 | 0.18 | 0.18 |

| | Turbidity by adsorption measurement at 540 nm [Au] | | | | | | | | | | | | | | |
|---|---|---|---|---|---|---|---|---|---|---|---|---|---|---|---|---|
| | #6 | | #6 + PS20 | | #3-1 | | #3-1+PS20 | | #3-2 | | #3-2+PS20 | | #3-3 | | #3-3+PS20 | |
| | n1 | n2 | n1 | n2 | n1 | n2 | n1 | n2 | n1 | n2 | n1 | n2 | n1 | n2 | n1 | n2 |
| T0 | 0.02 | 0.03 | 0.03 | 0.03 | 0.02 | 0.02 | 0.02 | 0.02 | 0.02 | 0.01 | 0.02 | 0.01 | 0.02 | 0.03 | 0.02 | 0.01 |
| Freeze/Thaw | 0.02 | 0.03 | 0.01 | 0.03 | 0.05 | 0.02 | 0.02 | 0.02 | 0.02 | 0.02 | 0.02 | 0.02 | 0.02 | 0.03 | 0.02 | 0.02 |
| Light stress | 0.03 | 0.03 | 0.03 | 0.03 | 0.04 | 0.03 | 0.03 | 0.03 | 0.03 | 0.04 | 0.03 | 0.03 | 0.04 | 0.01 | 0.04 | 0.04 |
| 1 week at 35°C + shaking | 0.03 | 0.03 | 0.04 | 0.03 | 0.03 | 0.03 | 0.02 | 0.03 | 0.03 | 0.04 | 0.02 | 0.03 | 0.03 | 0.03 | 0.03 | 0.03 |
| 2 weeks at 35°C + shaking | 0.04 | 0.04 | 0.02 | 0.03 | 0.03 | 0.03 | 0.02 | 0.02 | 0.06 | 0.04 | 0.02 | 0.03 | 0.27 | 0.04 | 0.03 | 0.03 |

| | Turbidity by adsorption measurement at 350 nm [Au] | | | | | |
|---|---|---|---|---|---|---|
| | #3-1+PS20+meth | | #3-2+PS20+meth | | #3-3+PS20+meth | |
| | n1 | n2 | n1 | n2 | n1 | n2 |
| Light stress | 0.24 | 0.22 | 0.26 | 0.25 | 0.42 | 0.38 |

Fig. 6

| | Concentration by UV 280 (mg/ml) | | | | | | | |
|---|---|---|---|---|---|---|---|---|
| | T0 | | 4 weeks | | 8 weeks | | 12 weeks | |
| | n1 | n2 | n1 | n2 | n1 | n2 | n1 | n2 |
| #3-1 + PS20 at 5 °C | 24 | 25 | 24 | 25 | 28 | 25 | 26 | 27 |
| #3-3 + PS20 at 5 °C | 25 | 25 | 24 | 25 | 25 | 25 | 27 | 27 |
| #3-1 + PS20 at 25 °C | 24 | 25 | 24 | 25 | 25 | 27 | 27 | 27 |
| #3-3 + PS20 at 25 °C | 25 | 25 | 24 | 24 | 25 | 26 | 27 | 28 |
| #3-1 + PS20 at 35 °C | 24 | 25 | 24 | 25 | 25 | 25 | 27 | 27 |
| #3-3 + PS20 at 35 °C | 25 | 25 | 25 | 23 | 27 | 25 | 28 | 27 |

| | Turbidity by nephelometry (NTU) | | | | | | | |
|---|---|---|---|---|---|---|---|---|
| | T0 | | 4 weeks | | 8 weeks | | 12 weeks | |
| | n1 | n2 | n1 | n2 | n1 | n2 | n1 | n2 |
| #3-1 + PS20 at 5 °C | 9.5 | 9.1 | 9.8 | 9.7 | 10.5 | 9.7 | 9.5 | 9.4 |
| #3-3 + PS20 at 5 °C | 11.5 | 11.7 | 11.7 | 12.1 | 12.0 | 11.5 | 11.8 | 12.2 |
| #3-1 + PS20 at 25 °C | 9.5 | 9.1 | 10.4 | 10.4 | 12.6 | 11.2 | 10.6 | 10.8 |
| #3-3 + PS20 at 25 °C | 11.5 | 11.7 | 13.0 | 12.1 | 13.3 | 12.4 | 11.5 | 11.7 |
| #3-1 + PS20 at 35 °C | 9.5 | 9.1 | 12.4 | 12.6 | 11.9 | 13.0 | 11.9 | 10.8 |
| #3-3 + PS20 at 35 °C | 11.5 | 11.7 | 12.7 | 12.4 | 15.3 | 15.2 | 13.1 | 13.8 |

| | rel. Main peak area by CZE [%] | | | | | | | |
| | T0 | | 4 weeks | | 8 weeks | | 12 weeks | |
| | n1 | n2 | n1 | n2 | n1 | n2 | n1 | n2 |
|---|---|---|---|---|---|---|---|---|
| #3-1 + PS20 at 5 °C | 40.5 | 39.7 | 39.7 | 39.4 | 38.0 | 37.3 | 38.9 | 39.2 |
| #3-3 + PS20 at 5 °C | 40.8 | 40.9 | 39.9 | 39.3 | 37.1 | 37.8 | 38.1 | 38.4 |
| #3-1 + PS20 at 25 °C | 40.5 | 39.7 | 38.8 | 38.6 | 36.6 | 36.6 | 37.5 | 36.9 |
| #3-3 + PS20 at 25 °C | 40.8 | 40.9 | 39.7 | 39.2 | 36.1 | 36.6 | 38.0 | 37.0 |
| #3-1 + PS20 at 35 °C | 40.5 | 39.7 | 38.2 | 38.7 | 35.8 | 34.8 | 24.1 | 24.2 |
| #3-3 + PS20 at 35 °C | 40.8 | 40.9 | 39.2 | 38.7 | 36.3 | 36.3 | 25.3 | 25.5 |

Fig. 18

Storage condition: 5 °C ± 3°C, upright

| Analytical parameter | Acceptable criteria | Analytical method | Initial | 1 Month | 3 Months | 6 Months | 9 Months | 12 Months | 18 Months |
|---|---|---|---|---|---|---|---|---|---|
| | | | | | Stability test interval | | | | |
| Appearance of the solution | Colour: colorless to slightly pink. | Ph. Eur., USP | Colorless solution | Colorless solution *) | Colorless solution *) | Colorless solution *) | Colorless solution *) | Colorless solution *) | Colorless solution *) |
| | Opalescence: Clear to slightly opalescent (≤ reference suspension III) | | Slightly opalescent **) | Slightly opalescent **) | Slightly opalescent **) | Slightly opalescent **) | Slightly opalescent **) | Slightly opalescent **) | Clear solution *) |
| | Presence of particles: solution essentially free from visible particles | | essentially free from visible particles | essentially free from visible particles | essentially free from visible particles | essentially free from visible particles | essentially free from visible particles | essentially free from visible particles | essentially free from visible particles |
| pH | 6.0 ± 0.2 | Ph. Eur., USP | 6.1 | 6.1 | 6.1 | 6.1 | 6.0 | 6.0 | 6.2 |
| Osmolality | 310 - 410 mOsmol/kg | Ph. Eur., USP | 365 mOsm/kg | 359 mOsm/kg | 359 mOsm/kg | 361 mOsm/kg | 360 mOsm/kg | 360 mOsm/kg | 360 mOsm/kg |
| Sub-visible particles (HIAC) | $\geq$ 10 µm: $\leq$ 6000 /vial, $\geq$ 25 µm: $\leq$ 600 /vial | Ph. Eur., USP | $\geq$ 10 µm: 48/vial, $\geq$ 25 µm: 2 /vial | $\geq$ 10 µm: 142/vial, $\geq$ 25 µm: 2 /vial | $\geq$ 10 µm: 23/vial, $\geq$ 25 µm: 1/vial | $\geq$ 10 µm: 2/vial, $\geq$ 25 µm: 0/vial | $\geq$ 10 µm: 8/vial, $\geq$ 25 µm: 3/vial | $\geq$ 10 µm: 18/vial, $\geq$ 25 µm: 5/vial | $\geq$ 10 µm: 6/vial, $\geq$ 25 µm: 0/vial |
| Concentration | 22.5 - 27.5 mg/mL | UV spectrophotometry | 26.3 mg/mL | 25.3 mg/mL | 26.0 mg/mL | 25.5 mg/mL | 25.2 mg/mL | 25.1 mg/mL | 25.0 mg/mL |
| Purity | Target monomer $\geq$ 90%, Sum Aggregates and fragments $\leq$ 10 % | SE-HPLC | Monomer: 99%, Sum Aggregates and Fragments: 1% | Monomer: 99%, Sum Aggregates and Fragments: 1% | Monomer: 99%, Sum Aggregates and Fragments: 1% | Monomer: 99%, Sum Aggregates and Fragments: 1% | Monomer: 99%, Sum Aggregates and Fragments: 1% | Monomer: 99%, Sum Aggregates and Fragments: 1% | Monomer: 99%, Sum Aggregates and Fragments: 1% |
| Purity | Isoform 1: pI 7.5 ±0.3, area $\geq$ 4.0%, Isoform 2: pI 7.7 ±0.3, area $\geq$ 40%, Isoform 3: pI 7.9 ±0.3, area $\geq$ 15.0%, Isoform 4: pI 8.1 ±0.3, area $\geq$ 4.0% Any unspecified peak, area $\leq$ 10 % | cIEF electrophoresis | pI: 7.52, A%: 6.802; pI: 7.71 A%: 55.542; pI: 7.96, A%: 27.181; pI: 8.21, A%: 10.476 | pI: 7.51, A%: 6.482; pI: 7.70, A%: 55.762; pI: 7.95, A%: 27.210; pI: 8.20, A%: 10.547 | pI: 7.54, A%: 7.425; pI: 7.75, A%: 54.578; pI: 7.99, A%: 27.637; pI: 8.25, A%: 10.360 | pI: 7.53, A%: 6.956; pI: 7.73, A%: 56.015; pI: 7.97, A%: 26.844; pI: 8.23, A%: 10.186 | pI: 7.52, A%: 7.454; pI: 7.72, A%: 55.261; pI: 7.96, A%: 27.041; pI: 8.21, A%: 10.244 | pI: 7.53, A%: 7.507; pI: 7.73, A%: 55.350; pI: 7.96, A%: 26.891; pI: 8.21, A%: 10.253 | pI: 7.55, A%: 7.765; pI: 7.75, A%: 55.064; pI: 7.97, A%: 26.790; pI: 8.23, A%: 10.381 |

*) comparable to water

**) comparable to reference suspension II

SEQUENCE LISTING

<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<223> OTHER INFORMATION: Heavy chain CDR

<400> SEQUENCE: 1

Thr Ser Gly Met Gly Ile Gly
1               5

<210> SEQ ID NO 2
<211> LENGTH: 16
<212> TYPE: PRT
<213> ORGANISM: Artificial Sequence
<220> FEATURE:
<223> OTHER INFORMATION: Heavy chain CDR

<400> SEQUENCE: 2

His Ala Trp Trp Asp Asp Asp Lys Arg Tyr Asn Pro Ala Leu Lys Ser
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Heavy chain CDR

<400> SEQUENCE: 3

His Tyr Gly Tyr Asp Pro Tyr Tyr Ala Met Asp Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Light chain CDR

<400> SEQUENCE: 4

Thr Ala Ser Ser Ser Val Ser Ser Ser Tyr Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Light chain CDR

<400> SEQUENCE: 5

Arg Thr Ser Asn Leu Ala Ser
1               5

-continued

<210> SEQ ID NO 6
<211> LENGTH: 9
<212> TYPE: PRT
<213> ORGANISM: Artificial Sequence
<220> FEATURE:
<223> OTHER INFORMATION: Light chain CDR

<400> SEQUENCE: 6

His Gln Tyr His Arg Ser Pro Pro Thr
1               5

<210> SEQ ID NO 7
<211> LENGTH: 449
<212> TYPE: PRT
<213> ORGANISM: Artificial Sequence
<220> FEATURE:
<223> OTHER INFORMATION: Heavy chain of humanized monoclonal antibody
      bexmarilimab

<400> SEQUENCE: 7

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
                20                  25                  30

Gly Met Gly Ile Gly Trp Ile Arg Gln Pro Pro Gly Lys Ala Leu Glu
            35                  40                  45

Trp Leu Ala His Ile Trp Trp Asp Asp Asp Lys Arg Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg His Tyr Gly Tyr Asp Pro Tyr Tyr Ala Met Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val

-continued

```
       290              295              300

Val Ser Val Leu Thr Val Leu His Gln Asp Trp Leu Asn Gly Lys Glu
305              310              315              320

Tyr Lys Cys Lys Val Ser Asn Lys Gly Leu Pro Ser Ser Ile Glu Lys
             325              330              335

Thr Ile Ser Lys Ala Lys Gly Gln Pro Arg Glu Pro Gln Val Tyr Thr
             340              345              350

Leu Pro Pro Ser Gln Glu Glu Met Thr Lys Asn Gln Val Ser Leu Thr
             355              360              365

Cys Leu Val Lys Gly Phe Tyr Pro Ser Asp Ile Ala Val Glu Trp Glu
             370              375              380

Ser Asn Gly Gln Pro Glu Asn Asn Tyr Lys Thr Thr Pro Pro Val Leu
385              390              395              400

Asp Ser Asp Gly Ser Phe Phe Leu Tyr Ser Arg Leu Thr Val Asp Lys
             405              410              415

Ser Arg Trp Gln Glu Gly Asn Val Phe Ser Cys Ser Val Met His Glu
             420              425              430

Ala Leu His Asn His Tyr Thr Gln Lys Ser Leu Ser Leu Ser Leu Gly
             435              440              445

Lys
```

```
<210> SEQ ID NO 8
<211> LENGTH: 215
<212> TYPE: PRT
<213> ORGANISM: Artificial Sequence
<220> FEATURE:
<223> OTHER INFORMATION: Light chain of humanized monoclonal antibody
      bexmarilimab

<400> SEQUENCE: 8

Glu Ile Val Leu Thr Gln Ser Pro Gly Thr Leu Ser Leu Ser Pro Gly
1               5               10               15

Glu Arg Ala Thr Leu Ser Cys Thr Ala Ser Ser Ser Val Ser Ser Ser
             20              25              30

Tyr Leu His Trp Tyr Gln Gln Lys Pro Gly Lys Ala Pro Lys Leu Leu
             35              40              45

Ile Tyr Arg Thr Ser Asn Leu Ala Ser Gly Val Pro Ser Arg Phe Ser
             50              55              60

Gly Ser Gly Ser Gly Thr Asp Tyr Thr Leu Thr Ile Ser Ser Leu Gln
65              70              75              80

Pro Glu Asp Phe Ala Thr Tyr Tyr Cys His Gln Tyr His Arg Ser Pro
             85              90              95

Pro Thr Phe Gly Gln Gly Thr Lys Leu Glu Ile Lys Arg Thr Val Ala
             100             105             110

Ala Pro Ser Val Phe Ile Phe Pro Pro Ser Asp Glu Gln Leu Lys Ser
             115             120             125

Gly Thr Ala Ser Val Val Cys Leu Leu Asn Asn Phe Tyr Pro Arg Glu
             130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
             165             170             175

Ser Ser Thr Leu Thr Leu Ser Lys Ala Asp Tyr Glu Lys His Lys Val
             180             185             190

Tyr Ala Cys Glu Val Thr His Gln Gly Leu Ser Ser Pro Val Thr Lys
```

-continued

```
            195                 200                 205

Ser Phe Asn Arg Gly Glu Cys
    210                 215
```

```
<210> SEQ ID NO 9
<211> LENGTH: 122
<212> TYPE: PRT
<213> ORGANISM: Artificial Sequence
<220> FEATURE:
<223> OTHER INFORMATION: Heavy chain variable region of humanized
      monoclonal antibody bexmarilimab

<400> SEQUENCE: 9

Gln Val Thr Leu Lys Glu Ser Gly Pro Thr Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Ile Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg His Tyr Gly Tyr Asp Pro Tyr Tyr Ala Met Asp Tyr Trp
            100                 105                 110

Gly Gln Gly Thr Leu Val Thr Val Ser Ser
        115                 120
```

```
<210> SEQ ID NO 10
<211> LENGTH: 108
<212> TYPE: PRT
<213> ORGANISM: Artificial Sequence
<220> FEATURE:
<223> OTHER INFORMATION: Light chain variable region of humanized
      monoclonal antibody bexmarilimab

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys
            100                 105
```

STABLE ANTI-CLEVER-1 ANTIBODY FORMULATION

This application is a 35 U.S.C. 371 National Phase Entry Application from PCT/FI/2021/050442 filed Jun. 14, 2021, which claims priority to and the benefit of Finish patent application No. 20205624, filed on Jun. 15, 2020, the disclosures of which are incorporated herein by reference in their entirety.

FIELD OF THE INVENTION

The present invention relates to stable formulations of an anti-CLEVER-1 antibody or antigen binding fragments thereof. The present invention further relates to stable formulations of an anti-CLEVER-1 antibody or antigen binding fragments thereof for use in treatment of various diseases and disorders.

BACKGROUND OF THE INVENTION

The human CLEVER-1 (Common Lymphatic Endothelial and Vascular Endothelial Receptor-1), is disclosed in the publication WO 03/057130. Clever-1 is also known as Stabilin-1 or Feel-1. The biology of CLEVER-1 has also been reviewed by Kzhyshkowska J. (2010), The Scientific World JOURNAL 10, 2039-2053, "Multifunctional receptor Stabilin-1 in homeostasis and disease". Clever-1 is expressed in lymphatic endothelial cells, certain vascular endothelial cells, but also in alternatively activated immunosuppressive macrophages e.g., tumour associated macrophages. It is also previously presented in the publication WO2010/122217 that blocking of CLEVER-1 by specific antibodies reduce the size of malignant tumour and/or malignant tumour growth. It is also previously presented e.g. in the publication WO2017/182705 that blocking of CLEVER-1 turns alternatively activated macrophages from an immunosuppressive (M2) phenotype to a pro-inflammatory (M1) phenotype.

The publication WO 03/057130 also discloses that CLEVER-1 mediates binding of other types of leukocytes such as monocytes and granulocytes to HEV-like vessels. Thus, by blocking the interaction of CLEVER-1 and malignant tumour cells it became possible to control metastasis by preventing malignant cells that bind to CLEVER-1 from being taken up by the lymphatic vessels, and thus to prevent spread of the malignancy into the lymph nodes.

Anti-CLEVER-1 antibodies are capable of inhibiting CLEVER-1 expression or binding to CLEVER-1 for blocking the function of CLEVER-1 or blocking the interaction of CLEVER-1 and cells involved with disease etiology.

Antibody drugs for use in humans may differ somewhat in the amino acid sequence of their constant domains, or in their framework sequences within the variable domains, but they typically differ most dramatically in the complementarity determining region (CDR) sequences. These differences result in different stabilities in a solution due to different responsiveness to the excipients in the solution or the pH of the solution. In addition, changes in the arrangement of amino acids or changes in one or a few amino acid residues can result in different antibody stability and susceptibility to sequence-specific degradation pathways. Further, antibodies for used as medicament in human subjects require storage prior to use and hence the stable formulation suitable for storage without affecting antibody functionality is also required.

SUMMARY OF THE INVENTION

An object of the present invention is to provide a stable formulation of an anti-CLEVER-1 antibody or antigen binding fragments thereof for pharmaceutical use, in which formulation of an anti-CLEVER-1 antibody or antigen binding fragments thereof will be stable during storage and hence has a sufficient long shelf-life for clinical use.

Further, the object of the present invention is to provide a pharmaceutical formulation comprising an anti-CLEVER-1 antibody or antigen binding fragments thereof with good colloidal and thermodynamic stability of protein, low aggregation during handling and storage, and low protein denaturation.

Further, an object of the present invention is to provide chemically stable formulation for preserving the functionality of the complementarity determining region (CDR) sequences of the anti-CLEVER-1 antibody and the efficacy of anti-CLEVER-1 antibody during storage.

In order to achieve among others the objects presented above, the invention is characterized by what is presented in the enclosed independent claims.

Some preferred embodiments of the invention will be described in the other claims.

The embodiments and advantages mentioned in this text relate, where applicable, both to the pharmaceutical formulation as well as to the uses according to the invention, even though it is not always specifically mentioned.

A typical stable pharmaceutical formulation according to the present invention comprises

- 1-100 mg/ml of an anti-CLEVER-1 antibody or antigen binding fragment(s) thereof,
- 5-50 mM of a histidine buffer in combination with 150-400 mM of trehalose, proline or mannitol as a stabilizing agent, wherein the pH of said pharmaceutical formulation is in the range of 5.5-6.5, or
- 5-50 mM of a Tris buffer in combination with 100-200 mM of sodium chloride as a stabilizing agent, wherein the pH of said pharmaceutical formulation is in the range of 7.0-7.6, and
- 0.01-0.1% (w/v) of polysorbate as a non-ionic surfactant, wherein the anti-CLEVER-1 antibody or antigen binding fragment(s) thereof comprises the following sequences of complementarity determining regions (CDRs) of the heavy chain

```
CDR1:
                                    (SEQ ID NO: 1)
TSGMGIG,

CDR2:
                                    (SEQ ID NO: 2)
HIWWDDDKRYNPALKS,
and

CDR3:
                                    (SEQ ID NO: 3)
HYGYDPYYAMDY,
``` and
the following sequences of complementarity determining regions (CDRs) of of the light chain

```
CDR 1:
                                    (SEQ ID NO: 4)
TASSSVSSSYLH,
```

-continued

CDR 2:

(SEQ ID NO: 5)

RTSNLAS,
and

CDR 3:

(SEQ ID NO: 6)

HQYHRSPPT.

A stable pharmaceutical formulation according to an embodiment of the present invention is a liquid formulation comprising an anti-CLEVER-1 antibody or antigen binding fragment(s) thereof, a stabilizing agent and a histidine buffer in a pH of 5.5-6.5. Alternatively, a formulation according to the present invention may be in a lyophilised form made by lyophilizing a liquid composition comprising an anti-CLEVER-1 antibody or antigen binding fragment(s) thereof, a stabilizing agent and a histidine buffer in a pH of 5.5-6.5. A formulation according to another embodiment of the present invention is a liquid formulation comprising an anti-CLEVER-1 antibody or antigen binding fragment(s) thereof, a stabilizing agent and a Tris buffer in a pH of 7.0-7.6. Further, a formulation according to an embodiment of the present invention may be in a lyophilised form made by lyophilizing a liquid composition comprising an anti-CLEVER-1 antibody or antigen binding fragment(s) thereof, a stabilizing agent and a Tris buffer in a pH of 7.0-7.6. The present invention relates also an aqueous composition obtained by reconstituting a lyophilized formulation.

A pharmaceutical formulation according to the present invention is suitable for use as infusion or injection. A pharmaceutical formulation according to the present invention is particularly suitable for intravenous administration.

It has been observed that chemical denaturation seems to be the most critical degradation pathway of anti-CLEVER-1 antibodies. Hence, according to the present invention especially chemical degradation of anti-CLEVER-1 antibody is avoided by providing storage stable composition. Maintaining the stability of the antibody is also crucial for preserving the antibody's functionality and efficacy, which is now achieved by the formulation according to the present invention. Further, a pharmaceutical formulation according to the present invention provides colloidal and thermodynamic stability.

According to the present invention, anti-CLEVER-1 antibodies or antigen binding fragment(s) thereof include those which specifically bind to human CLEVER-1 or are capable of inhibiting CLEVER-1 expression. Anti-CLEVER-1 antibodies or antigen binding fragment(s) thereof can be used to increase, enhance, stimulate or up-regulate an immune response. The present invention also concerns a formulation comprising anti-CLEVER-1 antibodies or antigen binding fragment(s) thereof for use as a medicament. A pharmaceutical formulation according to the present invention can be used in removing immunosuppression. A pharmaceutical formulation according to the present invention is suitable for use in treating and/or preventing cancer. Further, a pharmaceutical formulation according to the present invention is suitable for use in a treatment of chronic infections and/or acute inflammatory infections leading to immune exhaustion. A pharmaceutical formulation according to the present invention can also be used as an adjuvant of vaccine. Further, a pharmaceutical formulation according to the present invention is suitable for use in a treatment of hypercholesterolemia, dyslipidemia and/or atherosclerotic cardiovascular disease.

Typically, a method of treatment according to the present invention comprises administering an effective amount of a pharmaceutical formulation according to the present invention in a patient. In certain embodiments, the effective amount comprises a dose of anti-CLEVER-1 antibody or antigen binding fragment(s) thereof in the range 0.1-50 mg/kg, preferably in the range of 0.1-10 mg/kg.

BRIEF DESCRIPTION OF THE DRAWINGS

FIG. 1 shows the amino acid sequences of light and heavy chains of anti-CLEVER-1 antibody bexmarilimab according to a preferred embodiment of the present invention, FIG. 2-4 show the results of the concentration challenge test, namely concentration of the antibody, turbidity and the aggregate formation prior to the storage and after storage for one-week period at 5° C.±3° C. and at 35° C., FIGS. 5-9 show the results of forced degradation study, in which formulation variants have been exposed to light stress, thermal stress with agitation and freeze/thaw stress. Concentration of the antibody, turbidity, aggregate formation, the charge heterogeneity of the antibody and the oxidized degradation products have been analysed prior to the test and after exposed under the stress conditions, FIGS. 10-16 show the results of accelerated stability study at 5±3° C., 25° C. and 35° C., namely concentration of the antibody, turbidity, aggregate and fragment contents (SE-HPLC), the charge heterogeneity and the oxidized degradation products have been analysed prior to the storage, during storage and after 12 weeks storage, FIGS. 17-18 show the results of the stability study during and after 18 months storage at 5° C.±3° C.

DETAILED DESCRIPTION OF THE INVENTION

Figures 4, 5:
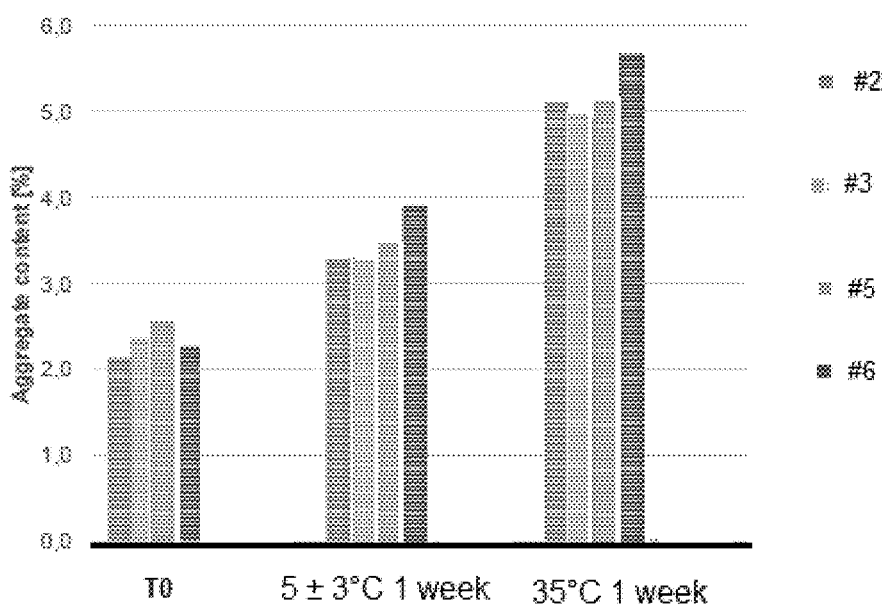

The present disclosure provides stable formulations of anti-CLEVER-1 antibody or antigen binding fragment(s) thereof that are biologically active. The term "biologically active" refers to an antibody or antibody fragment that is capable of binding CLEVER-1 and directly or indirectly exerting a biologic effect. A pharmaceutical formulation according to the invention comprises at least pharmacologically effective amount of anti-CLEVER-1 antibody or antigen binding fragment(s) thereof, a buffer and a stabilizing agent. A pharmaceutical formulation according to the present invention comprises a histidine buffer or a Tris (2-amino-2-(hydroxymethyl)propane-1,3-diol) buffer. According to a preferred embodiment of the present invention a pharmaceutical formulation further comprises a surfactant and/or an antioxidant for further improving stability of the formulation.

As used herein, the term "anti-CLEVER-1 antibody or antigen binding fragments thereof" refers to any form of antibody or antigen binding fragment(s) thereof that exhibits the desired biological activity. Anti-CLEVER-1 antibody or antigen binding fragment(s) thereof refers to antibodies and fragment(s) thereof, peptides or the like, which are capable of inhibiting CLEVER-1 expression or binding to CLEVER-1 for blocking the function of CLEVER-1 or blocking the interaction of CLEVER-1 and cells involved with disease etiology. CLEVER-1 is previously disclosed detailed in the publication WO 03/057130. The term "anti-CLEVER-1 antibody or antigen binding fragment(s)

thereof" is used in the broadest sense and it shall be understood to include monoclonal, chimeric, humanized or primatized antibodies, as well as antibody fragments and single chain antibodies (e.g. Fab, Fv), so long they exhibit the desired biological activities.

Formulations of the present disclosure include an anti-CLEVER-1 antibody or antigen binding fragment(s) thereof that are biologically active. According to an embodiment of the present invention, an anti-CLEVER-1 antibody or antibody fragment(s) that is capable of binding to CLEVER-1 is capable of binding to the specific CLEVER-1 epitope and directly or indirectly exerting a biologic effect. According to the present invention, anti-CLEVER-1 antibody or antigen binding fragment(s) thereof comprises the following sequences of complementarity determining regions (CDRs) of the heavy chain:

```
CDR 1:
                        (SEQ ID NO: 1)
TSGMGIG,

CDR 2:
                        (SEQ ID NO: 2)
HIWWDDDKRYNPALKS,
and

CDR 3:
                        (SEQ ID NO: 3)
HYGYDPYYAMDY,
``` and
the following sequences of complementarity determining regions (CDRs) of the light chain:

```
CDR 1:
                        (SEQ ID NO: 4)
TASSSVSSSYLH,

CDR 2:
                        (SEQ ID NO: 5)
RTSNLAS,
and

CDR 3:
                        (SEQ ID NO: 6)
HQYHRSPPT.
```

In an embodiment according to the present invention, an anti-CLEVER-1 antibody is a humanized monoclonal anti-CLEVER-1 antibody. In an embodiment according to the present invention, an anti-CLEVER-1 antibody may be a humanized antibody based on the monoclonal antibody 3-372 disclosed in the patent publication WO 03/057130. According to an embodiment of the present invention an anti-CLEVER-1 antibody is a humanized monoclonal anti-CLEVER-1 antibody, previously presented in the patent publication WO2017/182705. In an embodiment according to the present invention, a humanized anti-CLEVER-1 antibody comprises the constant regions of human IgG4 heavy chain and kappa light chain. In an embodiment of the present invention a humanized anti-CLEVER-1 antibody comprises a heavy chain variable region comprising SEQ ID NO: 9 and a light chain variable region comprising SEQ ID NO: 10. In an embodiment according to the present invention, a humanized anti-CLEVER-1 antibody comprises the constant regions from human immunoglobulin G4 (IgG4) heavy chain and kappa light chain and a heavy chain variable region comprising SEQ ID NO: 9 and a light chain variable region comprising SEQ ID NO: 10. In an embodiment of the present invention the constant regions from human IgG4 heavy chain and kappa light chain may comprise the mutations, wherein there is one or more conservative amino acid substitutions. According to an embodiment of the present invention, the anti-CLEVER-1 antibody or antigen binding fragment(s) thereof comprises an amino acid sequence SEQ ID NO:7 of a heavy chain and an amino acid sequence SEQ ID NO:8 of a light chain. The amino acid sequences of heavy chain (SEQ ID NO:7) and light chain (SEQ ID NO:8) of anti-CLEVER-1 antibody according to a preferred embodiment of the present invention are also shown in FIG. 1.

In an embodiment of the present invention, the anti-CLEVER-1 antibody is a humanized monoclonal immunoglobulin G4K antibody bexmarilimab (International Nonproprietary Name (INN)) as disclosed in WHO Drug Information, Vol. 33, No. 4, pages 814-815 (2019) as proposed INN and in WHO Drug Information, Vol. 34, No. 3 (2020), pages 699-700 as recommended INN), or bexmarilimab variant or the antibody in a bexmarilimab biosimilar. Anti-CLEVER-1 antibody bexmarilimab is an exemplary antibody used in the stable formulation described herein. As used herein, "bexmarilimab" means the humanized IgG4 monoclonal antibody with the structure described in WHO Drug Information, Vol. 33, No. 4, pages 814-815 (2019) and WHO Drug Information, Vol. 34, No. 3 (2020). A humanized IgG4 monoclonal anti-CLEVER-1 antibody bexmarilimab comprises an amino acid sequence SEQ ID NO:7 of a heavy chain and an amino acid sequence SEQ ID NO:8 of a light chain. Anti-CLEVER-1 antibody bexmarilimab comprises the light and heavy chain CDRs mentioned above (SEQ ID NO:1-SEQ ID NO:6). The sequences presented in SEQ ID NO: 7 and SEQ ID NO:8 includes also heavy chain and light chain variable regions of the anti-CLEVER-1 antibody bexmarilimab, i.e. the amino acid sequences corresponding to SEQ ID NO:9 and SEQ ID NO: 10.

A bexmarilimab biosimilar means a biological product which is approved by a regulatory agency in any country for marketing as a bexmarilimab biosimilar. In an embodiment, a bexmarilimab biosimilar comprises a bexmarilimab variant as the drug substance. In an embodiment, a bexmarilimab biosimilar has substantially the same amino acid sequence of heavy and light chains as bexmarilimab. As used herein, a "bexmarilimab variant" means an antibody which comprises sequences of heavy chain and light chain that are identical to those in bexmarilimab (SEQ ID NO:7 and SEQ ID NO:8, respectively), except for having one or more conservative amino acid substitutions at positions that are located outside of the light chain CDRs and/or one or more conservative amino acid substitutions that are located outside of the heavy chain CDRs, e.g. the variant positions are located in the framework regions or the constant region. In other words, bexmarilimab and a bexmarilimab variant comprise identical CDR sequences, but differ from each other due to having a conservative amino acid substitution at other positions in their full-length light and heavy chain sequences. A bexmarilimab variant is substantially the same as bexmarilimab with respect to binding affinity to CLEVER-1.

According to an embodiment of the present invention, a cell line producing the anti-CLEVER-1 antibody bexmarilimab (FP-1305) has been deposited on 27 May 2020 under the terms of the Budapest Treaty on the International Recognition of the Deposit of Micro-organisms for the Purposes of Patent Procedure with the DSMZ-German Collection of Microorganisms and Cell Cultures GmbH, Inhoffenstrasse 7B, D-38124 Braunschweig, Germany, and has the accession number DSM ACC3361. The present invention is not to be limited in scope by the culture deposited, since the deposited embodiment is intended as a single illustration of one aspect of the invention and any culture that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

According to the present invention, a stable formulation may comprise 1-100 mg/ml of an anti-CLEVER-1 antibody or antigen binding fragment(s) thereof. According to embodiments of the present invention, a concentration of an anti-CLEVER-1 antibody or antigen binding fragment(s) thereof in the stable pharmaceutical formulation may be in the range of 1-100 mg/ml or 5-100 mg/ml. A pharmaceutical formulation according to an embodiment of the present invention may be a concentrate which means that it is diluted to desired concentration prior to administration. In some embodiments according to the present invention, a pharmaceutical formulation may comprise 10-100 mg/ml or 20-100 mg/ml, preferably 20-40 mg/ml and more preferably 20-30 mg/ml of an anti-CLEVER-1 antibody or antigen binding fragment(s) thereof. In some embodiments according to the present invention, a pharmaceutical formulation according to the present invention may be a concentrate, which comprises 1-100 mg/ml, preferably 10-100 mg/ml and more preferably 20-40 mg/ml or 20-30 mg/ml or about 25 mg/ml, such as 22.5-27.5 mg/ml of an anti-CLEVER-1 antibody or antigen binding fragment(s) thereof.

A stable pharmaceutical formulation according to the present invention comprises a histidine buffer or a Tris buffer. The term "buffer" encompasses those agents which maintain the solution pH in an acceptable range, i.e. provide enough buffer capacity. The pH is typically measured at 25° C. using standard glass bulb pH meter. As used herein, a pharmaceutical formulation comprising "a buffer at pH X" refers to a pharmaceutical formulation solution at pH X and comprising the buffer, i.e. the pH is intended to refer to the pH of the solution.

A stable formulation according to an embodiment of the present invention comprises a histidine buffer. A pH of the formulation according to the present invention comprising histidine buffer is adjusted to be in the range of 5.5-6.5. In an embodiment of the present invention, a pharmaceutical formulation comprises histidine buffer and has a pH between 5.5 and 6.2, and preferably between 5.8 and 6.2, and more preferably pH is about 6.0. It has been observed that an anti-CLEVER-1 antibody or antigen binding fragment(s) thereof has highest colloidal and thermodynamic stability in weakly acidic histidine buffer systems. Said pH ranges are also acceptable range for i.v. infusion or bolus injection(s). According to an embodiment of the present invention the histidine buffer comprises L-histidine. Further, a pharmaceutical formulation according to an embodiment of the present invention may comprise a sufficient quantity of hydrochloric acid and/or sodium hydroxide with histidine buffer, such as L-histidine buffer for adjusting pH in in the range from about 5.5 to about 6.5 or from about 5.5 to about 6.2, and preferably has a pH of about 5.8 to about 6.2, and more preferable has a pH about 6.0. L-histidine/HCl as a buffer covers neutral to slight acidic pH-ranges. In an embodiment according to the present invention, a buffer comprises histidine, preferably L-histidine, and HCl (hydrochloric acid), wherein the pH of the pharmaceutical formulation according to present invention is in the range of 5.5-6.5, preferably 5.5-6.2 or 5.8-6.2.

According to an embodiment of the present invention, the formulation comprises 5-50 mM of the histidine buffer, preferably 5-20 mM or 5-15 mM of the histidine buffer. In an embodiment of the present invention the formulation comprises about 10 mM of histidine buffer, such as 5-15 mM or 8-12 mM or 9-11 mM or 9.5-10.5 of histidine buffer. According to an embodiment of the present invention, a formulation comprises histidine buffer without sodium chloride.

According to another embodiment of the present invention, a pharmaceutical formulation comprises a Tris (tris (hydroxymethyl)aminomethane) buffer, such as Tris base or Tris hydrochloride, and has a pH between 7.0 and 7.6 or between 7.2 and 7.6 or between 7.3 and 7.5. In an embodiment according to the present invention, a pharmaceutical formulation comprises a Tris buffer and has a pH about 7.4. In an embodiment of the present invention, the formulation comprises 5-50 mM of the Tris buffer, preferably 5-20 mM or 5-15 mM of the Tris buffer. In an embodiment of the present invention the formulation comprises about 10 mM of Tris buffer, such as 5-15 mM or 8-12 mM or 9-11 mM or 9.5-10.5 of Tris buffer. Further, a pharmaceutical formulation according to an embodiment of the present invention may comprise a sufficient quantity of hydrochloric acid with Tris buffer for adjusting pH in the range from about 7.1 to about 7.6 or between 7.2 and 7.6 or between 7.3 and 7.5 or to a pH about 7.4.

A pharmaceutical formulation according to the present invention further comprises a stabilizing agent. A stabilizing agent is used for further increasing colloidal and thermodynamic stability. In an embodiment according to the present invention, a formulation comprises trehalose, proline or mannitol, preferably trehalose or proline as a stabilizing agent in combination with histidine buffer. In a preferred embodiment of the present invention, a stabilizing agent comprises trehalose, such as trehalose dihydrate in combination with histidine buffer. In an embodiment of the present invention, the formulation comprises 150-400 mM, preferably 200-360 mM of trehalose, proline or mannitol as a stabilizing agent. In an embodiment of the present invention, the stabilizing agent comprises 150-400 mM, preferably 200-360 mM of trehalose, proline or mannitol. According to an embodiment of the present invention, the stabilizing agent comprises 220-340 mM or 240-320 mM of trehalose, proline or mannitol, preferably trehalose or proline, more preferably the stabilizing agent comprises 260-300 mM or 270-290 mM or about 280 mM of trehalose, proline or mannitol, preferably trehalose or proline. In a preferred embodiment according to the present invention a pharmaceutical formulation comprises trehalose, proline or mannitol as a stabilizing agent, preferably trehalose or proline as a stabilizing agent and more preferably trehalose, such as trehalose dihydrate as a stabilizing agent in combination with histidine buffer. In an embodiment of the present invention, the pharmaceutical formulation comprises 150-400 mM, preferably 200-360 mM of trehalose, proline or mannitol as a stabilizing agent in combination with histidine buffer. According to an embodiment of the present invention, the pharmaceutical formulation comprises 220-340 mM or 240-320 mM of trehalose, proline or mannitol as a stabilizing agent, preferably trehalose or proline as a stabilizing agent, more preferably the formulation comprises 260-300 mM or 270-290 mM or about 280 mM of trehalose, proline or mannitol, preferably trehalose or proline as a stabilizing agent. In an embodiment of the present invention about 280 mM of stabilizing agent may be about 275-285 mM of trehalose, proline or mannitol, preferably trehalose or proline.

In an embodiment according to the present invention, a stabilizing agent comprises sodium chloride, when a formulation comprises a Tris buffer. In an embodiment of the present invention, the formulation comprises a Tris buffer and sodium chloride as a stabilizing agent. In an embodiment of the present invention, a formulation comprises a Tris buffer in combination with 100-200 mM, preferably 130-180 mM or 140-160 mM of sodium chloride as a stabilizing agent. According to an embodiment of the present invention, a formulation comprises 100-200 mM, preferably 130-180 mM or 140-160 mM of sodium chloride as a stabilizing agent in combination with Tris buffer. According to an embodiment of the present invention, the formulation comprises about 150 mM of sodium chloride as a stabilizing agent in combination with Tris buffer. In an embodiment of the present invention about 150 mM of stabilizing agent may be about 145-155 mM of sodium chloride as a stabilizing agent in combination with Tris buffer.

A pharmaceutical formulation according to an embodiment of the present invention may further comprise a surfactant, preferably the surfactant comprises polysorbate and more preferably the surfactant comprises polysorbate 20. In an embodiment of the present invention, the formulation comprises polysorbate and preferably polysorbate 20 as a non-ionic surfactant. In an embodiment of the present invention, the formulation comprises 0.01-0.1% (w/v), preferably 0.01-0.05% (w/v) of a non-ionic surfactant. In an embodiment of the present invention, the formulation comprises 0.01-0.1% (w/v), preferably 0.01-0.05% (w/v) of polysorbate, preferably polysorbate 20. According to an embodiment of the present invention, the formulation comprises 0.01-0.03% (w/v) of polysorbate, preferably polysorbate 20. In an embodiment of the present invention, the formulation comprises about 0.02% (w/v), such as 0.015-0.025% (w/v) of polysorbate, preferably polysorbate 20. An addition of a non-ionic surfactant, such as polysorbate 20 provides increased stability, which can be observed lower turbidity during storage. Further, non-ionic surfactant, such as polysorbate 20 is used as a surfactant to facilitate the formulation process and to further stabilize the molecule in liquid formulation.

A pharmaceutical formulation according to an embodiment of the present invention may further comprise an antioxidant, preferably an antioxidant comprises L-methionine for further improving the stability of the formulation. The addition of methionine showed a slight improved stabilizing effect. In an embodiment of the present invention, the formulation comprises 5-40 mM, preferably 15-25 mM or 18-22 mM of antioxidant. In an embodiment of the present invention, the formulation comprises 5-40 mM, preferably 15-25 mM or 18-22 mM of L-methionine as an antioxidant. In an embodiment of the present invention, the formulation comprises about 20 mM of antioxidant, preferably L-methionine. In an embodiment of the formulation, about 20 mM of antioxidant, preferably L-methionine may be 19-21 mM or 19.5-20.5 mM of antioxidant, preferably L-methionine.

According to an embodiment of the present invention, a stable pharmaceutical formulation comprises 1-100 mg/ml of an anti-CLEVER-1 antibody or antigen binding fragment(s) thereof, a histidine or Tris buffer, a stabilizing agent, a surfactant and an antioxidant. In one embodiment according to the present invention, a stable pharmaceutical formulation comprises 1-100 mg/ml of an anti-CLEVER-1 antibody or antigen binding fragment(s) thereof, a histidine buffer, trehalose or proline as a stabilizing agent, a surfactant and an antioxidant. In another embodiment according to the present invention, a stable pharmaceutical formulation comprises 1-100 mg/ml of an anti-CLEVER-1 antibody or antigen binding fragment(s) thereof, a Tris buffer, sodium chloride as a stabilizing agent, a surfactant and an antioxidant. In one embodiment of the present invention, the formulation comprises:

(i) 1-100 mg/ml of an anti-CLEVER-1 antibody or antigen binding fragment(s) thereof, (ii) 5-50 mM of histidine buffer, (iii) 150-400 mM of trehalose, proline or mannitol as a stabilizing agent, (iv) 0.01-0.1% (w/v) of polysorbate 20 as a non-ionic surfactant, and (v) 5-40 mM of L-methionine as an antioxidant, wherein the pH of said composition is between 5.5 and 6.5, preferably between 5.8 and 6.2, and wherein the anti-CLEVER-1 antibody or antigen binding fragment(s) thereof comprises the following sequences of complementarity determining regions (CDRs) of the heavy chain

```
        CDR 1:
                                    (SEQ ID NO: 1)
        TSGMGIG,

CDR 2:
                                    (SEQ ID NO: 2)
        HIWWDDDKRYNPALKS,
        and CDR 3:
                                    (SEQ ID NO: 3)
        HYGYDPYYAMDY,
``` and
the following sequences of complementarity determining regions (CDRs) of of the light chain

```
        CDR 1:
                                    (SEQ ID NO: 4)
        TASSSVSSSYLH,

CDR 2:
                                    (SEQ ID NO: 5)
        RTSNLAS,
        and

CDR 3:
                                    (SEQ ID NO: 6)
        HQYHRSPPT,
``` and preferably the anti-CLEVER-1 antibody is the anti-CLEVER-1 antibody comprising the heavy chain SEQ ID NO: 7 and the light chain SEQ ID NO: 8.

According to an embodiment of the present invention, the formulation comprises:

(i) 20-40 mg/ml or 20-30 mg/ml of an anti-CLEVER-1 antibody or antigen binding fragment(s) thereof, (ii) 5-20 mM or 5-15 mM of histidine buffer, (iii) 200-360 mM, preferably 240-320 mM or 260-290 mM of trehalose, proline or mannitol as a stabilizing agent, (iv) 0.01-0.1% (w/v), preferably 0-01-0.05% (w/v) of polysorbate 20 as a non-ionic surfactant, and (v) 5-40 mM of L-methionine as an antioxidant, wherein the pH of said composition is between 5.5 and 6.5, preferably between 5.8 and 6.2, and wherein the anti-CLEVER-1 antibody or antigen binding fragment thereof comprises the following sequences of complementarity determining regions (CDRs) of the heavy chain

```
CDR 1:
                              (SEQ ID NO: 1)
TSGMGIG,

CDR 2:
                              (SEQ ID NO: 2)
HIWWDDDKRYNPALKS,
and

CDR 3:
                              (SEQ ID NO: 3)
HYGYDPYYAMDY,
``` and
the following sequences of complementarity determining regions (CDRs) of of the light chain

```
CDR 1:
                              (SEQ ID NO: 4)
TASSSVSSSYLH,

CDR 2:
                              (SEQ ID NO: 5)
RTSNLAS,
and

CDR 3:
                              (SEQ ID NO: 6)
HQYHRSPPT,
``` and preferably the anti-CLEVER-1 antibody is the anti-CLEVER-1 antibody comprising the heavy chain SEQ ID NO: 7 and the light chain SEQ ID NO: 8.

In one embodiment of the present invention, the formulation comprises:

(i) 1-100 mg/ml of an anti-CLEVER-1 antibody or antigen binding fragment(s) thereof, (ii) 5-50 mM of Tris buffer, preferably 5-20 mM or 5-15 mM of Tris buffer, (iii) 100-200 mM, preferably 130-180 mM of sodium chloride as a stabilizing agent, (iv) 0.01-0.1% (w/v), preferably 0-01-0.05% (w/v) of polysorbate 20 as a non-ionic surfactant, and (v) 5-40 mM of L-methionine as an antioxidant, wherein the pH of said composition is between 7.0 and 7.6, and
wherein the anti-CLEVER-1 antibody or antigen binding fragment thereof comprises the following sequences of complementarity determining regions (CDRs) of the heavy chain

```
CDR 1:
                              (SEQ ID NO: 1)
TSGMGIG,

CDR 2:
                              (SEQ ID NO: 2)
HIWWDDDKRYNPALKS,
and

CDR 3:
                              (SEQ ID NO: 3)
HYGYDPYYAMDY,
``` and
the following sequences of complementarity determining regions (CDRs) of of the light chain

```
CDR 1:
                              (SEQ ID NO: 4)
TASSSVSSSYLH,

CDR 2:
                              (SEQ ID NO: 5)
RTSNLAS,
and

CDR 3:
                              (SEQ ID NO: 6)
HQYHRSPPT,
``` and preferably the anti-CLEVER-1 antibody is the anti-CLEVER-1 antibody comprising the heavy chain SEQ ID NO: 7 and the light chain SEQ ID NO: 8.

In one preferred embodiment, the formulation according to the present invention comprises (i) 1-100 mg/ml, of anti-CLEVER-1 antibody or antigen binding fragment(s) thereof, (ii) 10 mM of L-histidine-HCl buffer, (iii) 280 mM of trehalose or proline, preferably 280 mM of trehalose or trehalose dihydrate as a stabilizing agent, (iv) 0.02% (w/v) of polysorbate 20 as a non-ionic surfactant, and (v) 20 mM of L-methionine as an antioxidant, wherein the pH of said composition is between 5.8 and 6.2 and
wherein the anti-CLEVER-1 antibody or antigen binding fragment thereof comprises the following sequences of complementarity determining regions (CDRs) of the heavy chain

```
CDR 1:
                              (SEQ ID NO: 1)
TSGMGIG,

CDR 2:
                              (SEQ ID NO: 2)
HIWWDDDKRYNPALKS,
and

CDR 3:
                              (SEQ ID NO: 3)
HYGYDPYYAMDY,
``` and
the following sequences of complementarity determining regions (CDRs) of of the light chain

```
CDR 1:
                              (SEQ ID NO: 4)
TASSSVSSSYLH,

CDR 2:
                              (SEQ ID NO: 5)
RTSNLAS,
and

CDR 3:
                              (SEQ ID NO: 6)
HQYHRSPPT,
``` and preferably the anti-CLEVER-1 antibody is the anti-CLEVER-1 antibody comprising the heavy chain SEQ ID NO: 7 and the light chain SEQ ID NO: 8.

More preferably, in one embodiment according to the present invention, a pharmaceutical formulation comprises (i) 20-40 mg/ml or 20-30 mg/ml or 25 mg/ml±2.5 mg/ml of anti-CLEVER-1 antibody or antigen binding fragment(s) thereof, (ii) 10 mM of L-histidine-HCl buffer, (iii) 280 mM of trehalose or proline, preferably 280 mM of trehalose or trehalose dihydrate as a stabilizing agent, (iv) 0.02% (w/v) of polysorbate 20 as a non-ionic surfactant, and (v) 20 mM of L-methionine as an antioxidant, wherein the pH of said composition is between 5.8 and 6.2, and wherein the anti-CLEVER-1 antibody or antigen binding fragment thereof comprises the following sequences of complementarity determining regions (CDRs) of the heavy chain

```
CDR 1:
                                   (SEQ ID NO: 1)
TSGMGIG,

CDR 2:
                                   (SEQ ID NO: 2)
HIWWDDDKRYNPALKS,
and

CDR 3:
                                   (SEQ ID NO: 3)
HYGYDPYYAMDY,
``` and
the following sequences of complementarity determining regions (CDRs) of of the light chain

```
CDR 1:
                                   (SEQ ID NO: 4)
TASSSVSSSYLH,

CDR 2:
                                   (SEQ ID NO: 5)
RTSNLAS,
and

CDR 3:
                                   (SEQ ID NO: 6)
HQYHRSPPT,
``` and preferably the anti-CLEVER-1 antibody is the anti-CLEVER-1 antibody comprising the heavy chain SEQ ID NO: 7 and the light chain SEQ ID NO: 8.

A formulation according to the present invention is preferably a liquid formulation.

According to an exemplary embodiment of the present invention, a liquid antibody formulation can be made by taking the anti-CLEVER-1 antibody in liquid form and buffer exchanging it into the desired formulation. There is no lyophilization step in this embodiment. The drug substance in the final buffer is concentrated to a desired concentration. Excipients, such as trehalose dihydrate and polysorbate 20 are added to the solution and it is diluted using the appropriate buffer to final protein concentration. The final formulated drug substance is filtered using 0.22 μm filters and filled into a final container (e.g. glass vials).

According to an embodiment of the present invention, a formulation can also be a lyophilized formulation, i.e. lyophilisate. The term "lyophilisate" refers to the product of lyophilisation. The term "lyophilize" with regard to pharmaceutical formulations of the invention is intended to refer to freeze drying of a solution of the formulation. Lyophilized formulations of therapeutic proteins may provide advantages, such as better chemical stability. A lyophilized formulation may also be reconstituted at different concentrations depending on clinical factors, such as route of administration or dosing. The term "reconstitution" refers to dissolution of the lyophilisate for achieving an aqueous solution.

It has been observed that pharmaceutical formulation according to the present invention stabilize anti-CLEVER-1 antibodies or antigen binding fragment(s) thereof against degradation during storage. According to an embodiment of the present invention a formulation comprising an anti-CLEVER-1 antibody or antigen binding fragment(s) thereof has storage stability at 2-8° C. A good stability at high concentrations, even at concentrations of 100 mg/ml of anti-CLEVER-1 antibodies or antigen binding fragment(s) thereof can be achieved. A "stable" pharmaceutical formulation according to the present invention is a pharmaceutical formulation comprising an anti-CLEVER-1 antibody or antigen binding fragment(s) thereof with no significant changes observed at a refrigerated temperature 2-8° C. for at least 3 months. The formulation according to the invention has been observed to be storage stable at temperature of 2-8° C. for at least 18 months or 24 months. A pharmaceutical formulation is considered to be storage stable at temperature of 2-8° C. for even at least 30 months and even a period of 36 months.

An antibody "retains its physical stability" in a pharmaceutical formulation if it shows no significant increase of aggregation and/or denaturation as measured by SE-HPLC, and/or no significant increase of colour and/or clarity. An antibody "retains its chemical stability" in a pharmaceutical formulation if it shows no significant chemical alteration. Chemical stability can be assessed by detecting and quantifying chemically altered forms of the protein. An antibody "retains its biological activity" in a pharmaceutical formulation, if the biological activity of the antibody at a given time is within a predetermined range of the biological activity exhibited at the time the pharmaceutical formulation was prepared. The biological activity of an antibody can be determined, for example, by an antigen binding assay. Typical acceptable criteria for stability are as follows. Typically, no more than about 10%, preferably about 5%, of antibody monomer is aggregated as measured by SE-HPLC. The pharmaceutical antibody formulation is colourless, or clear to slightly opalescent by visual analysis. The concentration has no more than +/−10% change. Typically, no more than about 10%, preferably about 5% of degradation or variant changes are observed. Potency is typically within 50-200% of the reference.

A pharmaceutical formulation of the invention can be administered into a patient. A formulation according to an embodiment of the present invention is targeted to intravenous or intratumoral administration. A formulation in a liquid form can be diluted prior to administration. A formulation in a lyophilized form can be reconstituted at different concentrations prior to dosing. According to one preferred embodiment of the invention a pharmaceutical formulation is administered intravenously. It can be administered via intravenous infusion or bolus injection. The term "intravenous" or 'IV' administration refers to administration into the blood vessels.

A formulation according to the present invention comprising anti-CLEVER-1 antibody or antibody fragment(s) thereof can be used as a medicament.

A formulation according to the present invention comprising anti-CLEVER-1 antibody or antibody fragment(s) thereof can be used in removing tumour or antigen induced immunosuppression. A pharmaceutical formulation according to the present invention is suitable for use in treating or preventing cancer. In an embodiment according to the present invention, a pharmaceutical formulation may shrink tumors or inhibit their growth or prevent metastasis. A pharmaceutical formulation is applicable to all forms of cancer. Any benign or malignant tumor or metastasis of malignant tumor can be treated. Also leukemias, lymphomas and multiple myelomas can be treated.

A formulation according to the present invention comprising anti-CLEVER-1 antibody or antibody fragment(s) thereof can also be used to treatment or prevention of chronic infections or acute inflammatory infections leading to immune exhaustion, wherein the modulation of macrophage phenotype is achieved by anti-CLEVER-1 antibody.

A pharmaceutical formulation according to the present invention may also be utilized as an adjuvant of vaccine. Anti-CLEVER-1 antibody achieve repolarization of macrophages and thus removes or at least decreases immune suppression against the vaccine antigens.

Further, a pharmaceutical formulation according to the present invention is suitable for use in a treatment of hypercholesterolemia, dyslipidemia and/or atherosclerotic cardiovascular disease, since it has also been observed that antibodies capable of binding to CLEVER-1 have also ability to inhibit and/or block modified low density lipoprotein, particularly acetylated low-density lipoprotein (acLDL), uptake by CLEVER-1 and becoming a foam cell, i.e. the precursor of an atherosclerotic plaque.

The term "treatment" or "treating" shall be understood to include complete curing of a disease as well as amelioration or alleviation of said disease. The term "prevention" shall be understood to include complete prevention, prophylaxis, as well as lowering the individual's risk of falling ill with said disease or disorder.

The dose of anti-CLEVER-1 antibody or antigen binding fragment(s) thereof chosen should be pharmacologically effective amount and hence sufficient to bring about a desired therapeutically result, e.g. to reduce malignant tumour growth and/or inhibit metastatic spread and/or to block the negative regulation of T cells in cancer, chronic infection, infectious diseases or other states of immune exhaustion. According to an embodiment of the present invention, anti-CLEVER-1 antibody is administered in the range of 0.1-50 mg/kg, preferably 0.1-30 mg/kg or 0.1-10 mg/kg, according to the patient's body weight. In an embodiment according to the present invention, anti-CLEVER-1 antibody is administered in the range of 0.3-10 mg/kg, and preferably 0.3-3 mg/kg, according to the patient's body weight. In an embodiment according to the present invention, a method for treating cancer, chronic infection, infectious diseases or other states of immune exhaustion comprises an administration of a pharmaceutical formulation according to the present invention, preferably in an amount of 0.1-50 mg/kg, preferably 0.1-30 mg/kg or 0.1-10 mg/kg, according to the patient's body weight.

A formulation according to the present invention comprising anti-CLEVER-1 antibody or antibody fragment(s) thereof can be used alone or in combination with other agents or pharmaceutical products. In an embodiment according to the present invention, a pharmaceutical formulation comprising an anti-CLEVER-1 antibody or antigen binding fragment(s) thereof is used in a treatment of cancer alone or in combination with other immunotherapeutics.

EXPERIMENTAL PART

In the present experimental part, stability of the pharmaceutical formulation according to the present invention comprising anti-CLEVER-1 antibody has been studied and confirmed.

Drug Substance

FP-1305 is a humanized monoclonal immunoglobulin G4K anti-CLEVER-1 antibody produced in CHO cells. More detailed FP-1305 is a humanized monoclonal anti-CLEVER-1 antibody bexmarilimab (International Nonproprietary Name (INN)) disclosed in WHO Drug Information, Vol. 33, No. 4, pages 814-815 (2019) as proposed INN and in WHO Drug Information, Vol. 34, No. 3 (2020), pages 699-700 as recommended INN). The amino acid sequences of the heavy and light chains of FP-1305 comprises SEQ ID NO:7 and SEQ ID NO:8 (presented also in FIG. 1). FP-1305 comprises CDR sequences SEQ ID NO:1-SEQ ID NO:6. The cell line for producing FP-1305 is deposited under accession number DSM ACC3361 at the DSMZ-German Collection of Microorganisms and Cell Cultures.

Analytical Methods

Analytical methods for evaluating formulation stability include dynamic laser light scattering test (DLS), nano differential scanning calorimetry (nanoDSC), composition gradient multi-angle light scattering (CG-MALS), SE-HPLC (size exclusion chromatography), reduced RP-HPLC and capillary zone electrophoresis (CZE). The standard methods of above-mentioned analysis are used.

DLS is used for determination of protein-protein interactions. At higher concentration of macromolecules, interactions between adjacent particles result in non-ideal diffusion behavior (intermolecular stability gets affected). This can be described by the second hydrodynamic virial coefficient $k_D$. The $k_D$-value describes the propensity for nonspecific molecular association under a given set of solution conditions. The onset temperature of thermal denaturation ($T_{onset}$), i.e. the starting point of the unfolding transition, (denaturation onset temperature can also be determined by DLS.

NanoDSC is specifically designed to determine the denaturation temperature ($T_{onset}$) and thermal denaturation enthalpy of proteins and other macromolecules in solution with the versatility and precision to perform molecular stability screenings.

In CG-MALS, interactions between protein molecules in solution were characterized by changes in their light scattering behavior at different concentrations. With this series of light scattering measurements, the second virial coefficient $A_2$, which is a characteristic parameter to measure molecule interactions, was calculated. A negative $A_2$ indicates attractive interactions between molecules of the dissolved substance whereas a positive $A_2$ is characteristic for repulsive interactions between the dissolved protein molecules.

SE-HPLC (size exclusion chromatography) is a standard method for the detection of aggregated and fragmented protein species.

Capillary zone electrophoresis (CZE) is a method for the analysis of charge heterogeneity of proteins in the native state. CZE was performed according to the standard methods.

Reduced RP-HPLC is a standard method for the detection of oxidized antibody species.

The concentration was determined by UV280 absorption measurement.

The absorption of the undiluted sample was measured at wavelength of 350 nm and 510 nm to identify increasing turbidity. The turbidity of the samples was also determined using a turbidity meter according to the European Pharmacopeia. In visual inspection, samples were examined visually under backlight.

Evaluating Buffer and pH Conditions of Anti-CLEVER-1 Formulation

Formulations presented in Table 1 were selected to study the general behavior of the drug substance FP-1305 regarding pH, buffer ingredient and ionic strength with respect to highest colloidal and thermodynamic stability of the protein. Samples were prepared by dialysis of FP-1305 (10-15 mg/mL) into said buffer system.

Protein-protein interactions as a measure for the colloidal stability in the buffer system were determined by measuring the hydrodynamic radius of FP-1305 with increasing concentration of FP-1305. The data were used to predict protein aggregation during handling and storage.

Denaturation temperature (thermodynamic stability) in buffer system was determined by measuring the hydrodynamic radius of FP-1305 with increasing temperature. Once protein domains began to denature, the hydrodynamic radius of the protein rose remarkably. The onset-temperature of unfolding could be taken as an indicator of the secondary structure stability of the protein. The data were used to predict protein denaturation during handling and storage.

The pH of the formulation was modulated from 5.5 to 7.4 (acceptable range for intravenous or bolus injections). The selected L-histidine buffer covers neutral to slight acidic pH-ranges. Tris buffer is tested as an alternative buffer component covering physiological pH regions. The pH was adjusted with a sufficient quantity of 6 N hydrochloric acid and, if needed, with 10 N sodium hydroxide.

The ionic strength (max ionic strength was set to isotonicity) of the formulations with Tris buffer was modulated by adding sodium chloride.

strength significantly reduces the repulsive interactions at low pH and should be avoided. Clear repulsive protein interactions were observed for histidine/HCl buffers without sodium chloride at pH 5.5 and 6.0. At pH 7.4 the addition of sodium chloride reduced the attractive interactions and was thus beneficial effect on the colloidal stability.

Thermodynamic stability is somewhat opposite to the colloidal stability. The addition of sodium chloride is beneficial for the thermodynamic stability in Tris buffer system. In the case of L-histidine/HCl, the addition of sodium chloride reduces the onset temperature of unfolding. Hence, the formulation with histidine buffer is preferably free of sodium chloride (NaCl).

On the basis of the findings of these tests, the formulation variants presented in Table 2 were selected and tested using CG-MALS, nano-DSC, DLS and SE-HPLC with the addition of the stabilizers trehalose, mannitol and L-proline at concentrations leading to isotonicity. Variant no. 6 was evaluated as alternative variant at physiologic pH. The results are presented in Table 3.

TABLE 2

Formulation variants.

| Variant no. | pH | Buffer | Stabilizer |
|---|---|---|---|
| 2-1 | 5.5 | 10 mM L-histidine/HCl | 280 mM trehalose |
| 2-2 | 5.5 | 10 mM L-histidine/HCl | 280 mM mannitol |
| 2-3 | 5.5 | 10 mM L-histidine/HCl | 280 mM proline |
| 3-1 | 6.0 | 10 mM L-histidine/HCl | 280 mM trehalose |
| 3-2 | 6.0 | 10 mM L-histidine/HCl | 280 mM mannitol |
| 3-3 | 6.0 | 10 mM L-histidine/HCl | 280 mM proline |
| 6 | 7.4 | 10 mM Tris/HCl | 150 mM NaCl |

TABLE 3

Results of the screening experiments with CG-MALS, nano-DSC, DLS and SE-HPLC

| Variant no. | Tonset Nano-DSC [° C.] | $A_2^+$ [$10^{-4}$ mol* mL*g$^{-2}$] | kd by DLS [$10^{-2}$ mL/mg] | Tonset DLS [° C.] | Relative aggreg. content [%] |
|---|---|---|---|---|---|
| 2-1 | 54 | 0.4 | 0.0 | 59 | 3.6 |
| 2-2 | 54 | 0.3 | −0.1 | 59 | 3.7 |
| 2-3 | 54 | 0.3 | 0.6 | 59 | 3.7 |
| 3-1 | 56 | 0.3 | −0.1 | 60 | 3.8 |
| 3-2 | 56 | −0.1 | −0.2 | 60 | 3.8 |
| 3-3 | 56 | 0.1 | 0.4 | 60 | 3.8 |
| 6 | 60 | −0.6 | −0.6 | 62 | 3.9 |

TABLE 1

Selected formulations and the results of nanoDSC and DLS

| Variant no. | pH | Buffer | Salt | Tonset [° C.] | kd [mL/mg*10$^{-2}$] |
|---|---|---|---|---|---|
| 1 | 5.5 | 10 mM L-histidine/HCl | 150 mM NaCl | 49 | −0.4 |
| 2 | 5.5 | 10 mM L-histidine/HCl | without | 55 | 0.8 |
| 3 | 6.0 | 10 mM histidine/HCl | without | 58 | 0.4 |
| 4 | 6.5 | 10 mM L-histidine/HCl | 150 mM NaCl | 52 | −0.6 |
| 5 | 6.5 | 10 mM L-histidine/HCl | without | 55 | −0.2 |
| 6 | 7.4 | 10 mM Tris/HCl | 150 mM NaCl | 61 | −0.5 |
| 7 | 7.4 | 10 mM Tris/HCl | without | 59 | −1.7 |

From the results presented in Table 1, it has been observed that the colloidal stability of FP-1305 is higher at acidic pH values compared to neutral pH values. However, high ionic The addition of the stabilizers to the L-histidine/HCl buffer systems had no remarkable influence on both the colloidal and thermodynamic stability. The interactions between the molecules were nearly zero (slightly repulsive to slightly attractive) in all cases.

Concentration Challenge Test

A broad pH range (the pH shows the strongest effect on colloidal and thermodynamic stability) was used without the addition of further stabilizers in the concentration challenge test. The tested variants are presented detailed in Table 1.

The concentration of FP-1305 drug substance was increased to 16 mg/mL using a crossflow instrument. The solution of FP-1305 was centrifuged at 4000 rpm for 5 min to remove any insoluble particles. Afterwards the solution was filtrated using a 0.22 μm membrane filter. Samples for the accelerated stability testing were prepared by dialyzing the concentrated FP-1305 drug substance (DS) into the selected buffer variants in three dialysis steps to achieve a quantitative buffer exchange. 50 mL of the DS with approximately 16 mg/mL were transferred into preconditioned (in dialysis buffer) dialysis tubes. Filled dialysis tubes were incubated in 1000 mL of the target buffer for 2 hours before a first buffer change (1000 mL) was performed. After dialysis for two further hours the buffer was changed a second time (1000 mL) to finalize the dialysis overnight.

Thereafter the solution was concentrated to about 100 mg/mL by ultrafiltration. After the concentration step the solutions were sterile filtered using a 0.22 μm syringe filter under laminar flow. 0.5 mL of the high-concentrated samples were filled into sterilized standard 2R glass vials. Samples were stored at 5±3° C. (2-8° C.) and 35° C. for 7 days. The samples were analyzed by UV at 280 nm, absorption measurement at 350 nm and 510 nm and SE-HPLC was performed before and after storage. Samples are also analyzed visually.

The results of the concentration determination using UV-280 nm are shown in FIG. 2. In all formulation variants FP-1305 concentrations above 100 mg/mL could be realized. During the short-term stability study of the high concentrated samples the concentration remained unchanged.

The results of the adsorption measurement at 350 nm and 510 nm are shown in FIG. 3. None of the formulation showed an increase in turbidity during the stability study neither at 5±3° C. nor at 35° C. In visual inspection, at the beginning of the stability study all formulations showed a clear, slightly red solution. After 7 days of storage both at 5±3° C. and at 35° C., none of the samples showed visible particles.

Soluble aggregate formation was detected by means of SE-HPLC, as described above in the analytical methods, in all formulation variants both at 5±3° C. and at 35° C., as shown in FIG. 4. At 35° C. aggregates evolved more rapidly than at 5±3° C. The aggregate formation was lower in L-histidine/HCl formulations compared to Tris/HCl formulation. There was no remarkable effect of the pH of the L-histidine formulations on aggregate formation with a tendency towards lower aggregate formation at more acidic pH, i.e. at pH 5.5 and pH 6.0.

Forced Degradation Study

Based on above stability study, the formulations presented in Table 4 selected for further testing in a forced degradation study to determine the formulation variants that exhibited the highest stability against multiple stress conditions (light stress, thermal stress with agitation and freeze/thaw stress). Formulations are prepared with or without polysorbate 20 (PS20). Additional light stress studies were performed with the variants 3-1+PS20, 3-2+PS20 and 3-3+PS20 with 20 mM of L-methionine added in the formulation to examine the stabilizing effect of L-methionine against chemical degradation induced by radicals.

TABLE 4

Formulations selected after concentration
challenge test for further testing.

| Variant no. | pH | Buffer | Stabilizer | Polysorbate 20 |
|---|---|---|---|---|
| 3-1 | 6.0 | 10 mM L-histidine/HCl | 280 mM trehalose | without |
| 3-1 + PS20 | 6.0 | 10 mM L-histidine/HCl | 280 mM trehalose | 0.02% |
| 3-2 | 6.0 | 10 mM L-histidine/HCl | 280 mM mannitol | without |
| 3-2 + PS20 | 6.0 | 10 mM L-histidine/HCl | 280 mM mannitol | 0.02% |

TABLE 4-continued

Formulations selected after concentration
challenge test for further testing.

| Variant no. | pH | Buffer | Stabilizer | Polysorbate 20 |
|---|---|---|---|---|
| 3-3 | 6.0 | 10 mM L-histidine/HCl | 280 mM proline | without |
| 3-3 + PS20 | 6.0 | 10 mM L-histidine/HCl | 280 mM proline | 0.02% |
| 6 | 7.4 | 10 mM Tris/HCl | 150 mM NaCl | without |
| 6 + PS20 | 7.4 | 10 mM Tris/HCl | 150 mM NaCl | 0.02% |

The concentration of FP-1305 drug substance was increased to 25 mg/mL using a crossflow instrument. The solution of FP-1305 was centrifuged at 4000 rpm for 5 min to remove any insoluble particles. Afterwards the solution was filtrated using a 0.22 μm membrane filter. Samples for the accelerated stability testing were prepared by dialyzing the concentrated FP-1305 drug substance into the selected buffer variants in three dialysis steps to achieve a quantitative buffer exchange: The dialysis of FP-1305 was accomplished in three dialysis steps to achieve a quantitative buffer exchange. 25 mL of the solution with approximately 25 mg/mL FP-1305 were transferred into preconditioned (in dialysis buffer) dialysis tubes. Filled dialysis tubes were incubated in 1000 mL of the target buffer for 2 hours before a first buffer change (1000 mL) was performed. After dialysis for two further hours the buffer was changed a second time (1000 mL) to finalize the dialysis overnight.

After the dialysis step the solutions were supplemented with polysorbate 20 or polysorbate 20 and L-methionine to achieve the desired formulation variants. Afterwards, the samples were sterile filtered using a 0.22 μm syringe filter under laminar flow. 0.8 mL of the samples were filled into sterilized standard 6R glass vials. The samples were exposed to the following stress conditions:

1) Forced thermal stress with agitation: Storage at 35° C. under agitation of 200 rpm.
2) Exposure to light: For 7.5 h at 750 W/m$^2$/25° C.
3) Freeze-thaw stress: Liquid samples were frozen from room temperature to −50° C. at a controlled freezing rate and warmed up again to room temperature at a controlled heating rate (1° C./min to simulate bulk freezing conditions).

Prior to and after each time point from each stress condition, two liquid samples of each variant were visually analyzed for precipitation. Samples were analyzed with respect to concentration by UV280 nm, turbidity by absorption measurement at 350 nm and 510 nm, aggregate status by SE-HPLC, chemical degradation by CZE and reduced RP-HPLC. The results are shown in FIGS. 5-9.

FIG. 5 shows the results of the concentration determination by UV-280 nm. Concentration of the samples remained constant in all variants. A solution of L-methionine was also added to the samples (variants 3-1+PS20+meth, 3-2+PS20+ meth and 3-3+PS20+meth) leading to a dilution. Target concentrations of these samples were around 24 mg/mL. The concentration was measured by UV 280 nm.

The results of the adsorption measurement at 350 nm and 510 nm are presented at FIG. 6. Freeze/thaw stress showed no increase in turbidity of the samples. The absorbance at 350 nm slightly increased after light stress. Some beneficial effect of polysorbate 20 was observed. Methionine does not have a beneficial effect on the turbidity after light stress. After 2 weeks at thermal stress some formulations showed turbidity (variants 3-2 and 3-3).

Visually clear samples were obtained in all formulation variants with polysorbate after freeze/thaw stress testing and after light stress. Thermal stress induced the formation of gel like particles. After 2 weeks of thermal stress, all variants with polysorbate 20 remained clear whereas all variants without polysorbate 20 contained gel like particles.

Figure 7:
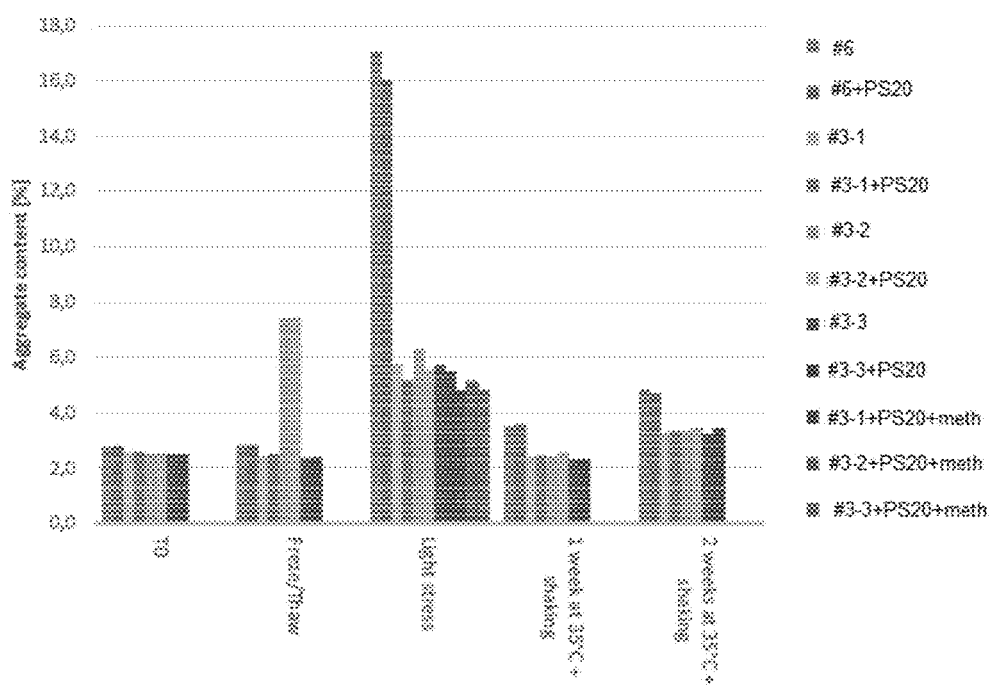

The possible aggregation was tested with SE-HPLC. FIG. 7 shows the aggregate content of the formulation variants at the beginning of the stability study and after each stress test (the bars in order from left to right corresponds variants mentioned from up to down in FIG. 7).

After freeze/thaw stress an increase in aggregation was observed for variants 3-2 and 3-2+PS20 comprising mannitol. A slight increase in aggregation was observed for variants 6 and 6+PS20 comprising Tris buffer. No additional aggregates were formed in other variants.

Light stress induced aggregation in all formulation variants with the lowest aggregation in variant 3-3 followed by variants 3-1, 3-2 and 6. Some minor beneficial effect of polysorbate 20 and L-methionine was observed. Aggregates increased in all formulations under thermal stress/agitation which was strongest in the variant 6. After 2 weeks at 35° C. the aggregate content rose in all formulation variants.

Figure 8:
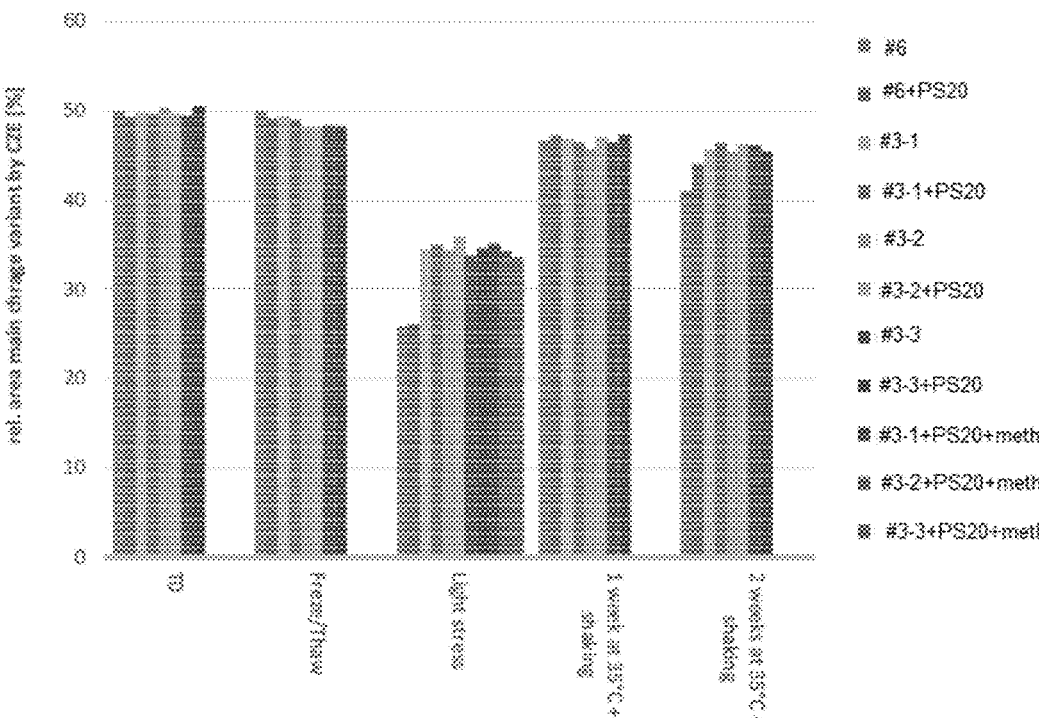

Capillary zone electrophoresis (CZE) was used to monitor the charge heterogeneity of the antibody and was a measure for the chemical stability of the sample. FIG. 8 shows the charge heterogeneity of the formulation variants at the beginning of the stability study and after each stress test (the bars in order from left to right corresponds variants mentioned from up to down in FIG. 8). After stress, acidic subvariants were formed being potentially deamidated subvariants and other charge heterogeneities. Freeze/thaw stress had only a slight effect on the charge heterogeneity of the samples. Highest degradation was observed after light stress. The degradation was higher for variant no. 6 compared to the other variants. Polysorbate 20 and methionine showed no remarkable effect on the chemical stability of FP-1305. Formation of charge variants was observed for all formulation variants during thermal stress. Highest stability was observed in all histidine/HCl buffer containing variants. The lowest stability was observed for variant no. 6 (Tris/HCl buffer). Polysorbate 20 showed neither a positive nor a negative effect on the stability of FP-1305 against chemical degradation.

Figures 9, 10, 11:
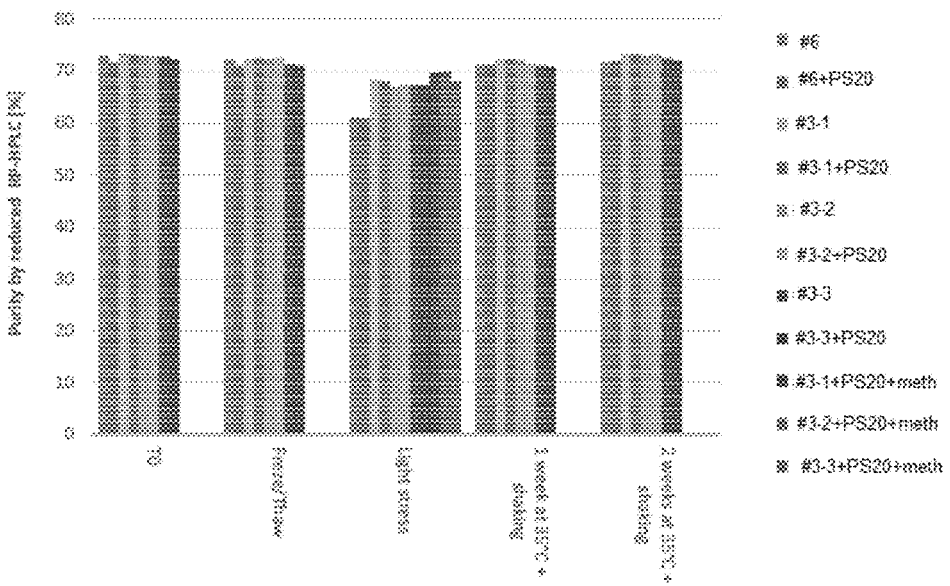

The samples were analyzed also with a reduced RP-HPLC to detect oxidized degradation products. FIG. 9 shows the purity by reduced RP-HPLC of the formulation variants at the beginning of the stability study and after each stress test (the bars in order from left to right corresponds variants mentioned from up to down in FIG. 9). No degradation/ oxidation was observed after freeze/thaw and thermal stress for up to 2 weeks at 35° C. with agitation. During light stress the purity of the samples dropped with the highest purity in variant 3-1 followed by variants 3-2, 3-3 and 6. Polysorbate 20 had no influence on the purity of FP-1305 by reduced RP HPLC. L-methionine showed a slightly positive effect on the purity of FP-1305 after light stress.

In conclusion, the histidine/HCl buffer system at pH 6.0 was preferred over the Tris/HCl buffer system due to the higher chemical stability and lower tendency for aggregation. However, Tris/HCl buffer system seems to provide an alternative for histidine/HCl buffer system although the stability of FP-1305 is better in slightly acidic histidine buffer system. Addition of polysorbate 20 proved to increase stability specifically under freeze/thaw stress as samples without polysorbate 20 showed turbidity after freeze/thaw testing. The stabilizers trehalose and proline were preferred over mannitol with histidine buffer because of higher stability during freeze/thaw stress. The addition of methionine showed a slight stabilizing effect on FP-1305 against radical induced degradation (formation of aggregates and impurities during light stress).

Accelerated Stability Studies

The two formulations presented at Table 5 were placed in accelerated stability studies for studying the stability of FP-1305 at 5° C.±3° C., 25° C. and 35° C.

TABLE 5

| Formulations for accelerated stability testing | | | | | |
|---|---|---|---|---|---|
| Variant no. | pH | Buffer | Stabilizer | Antioxidant | Surfactant |
| 3-1 + PS20 | 6.0 | 10 mM L-histidine/HCl | 280 mM trehalose | 20 mM L-methionine | 0.02% Polysorbate 20 |
| 3-3 + PS20 | 6.0 | 10 mM L-histidine/HCl | 280 mM proline | 20 mM L-methionine | 0.02% Polysorbate 20 |

The concentration of FP-1305 drug substance was increased to 25 mg/mL using a crossflow instrument. Samples for the accelerated stability testing were prepared by dialyzing the concentrated FP-1305 drug substance into the selected buffer variants in three dialysis steps to achieve a quantitative buffer exchange similar as disclosed above in relation to the forced degradation study. After the dialysis step the solutions were supplemented with a polysorbate 20 stock and L-methionine solution to obtain the desired formulation variants. Afterwards, the samples were sterile filtered using a 0.22 μm syringe filter under laminar flow. 1.4 mL of the samples were filled into sterilized standard 6R glass vials.

The samples were stored at 5° C.±3° C. (2-8° C.), 25° C.±2° C. and 35° C.±2° C. upside down without humidity control for 12 weeks. Two liquid samples were taken per time point (T0, T4 weeks, T8 weeks, T12 weeks) and temperature. All samples were analyzed at each time point separately with respect to concentration by UV at 280 nm, turbidity by nephelometric measurement, aggregate status by SE-HPLC and chemical degradation by reduced RP-HPLC and CZE. The results are shown in FIGS. 10-16.

FIG. 10 shows the results of the concentration determination by UV-280 nm. The concentration of the samples remained constant during the stability testing independent of the storage temperature and formulation. Also, the samples of all formulation variants remained clear during the stability study independent of the storage temperature as inspected visually.

FIG. 11 shows the results of the nephelometric turbidity measurement. The turbidity of the samples remained constant during the stability testing at 5° C.±3° C. and 25° C. At 35° C. a slight increase in turbidity was observed for both formulation variants. Formulation variant 3-1+PS20 was slightly less turbid than formulation variant 3-3+PS20. Increased turbidity is a sign for the formation of insoluble aggregates. However, the turbidity of the samples was relatively low even after 12 weeks at 35° C. After 12 weeks, a slight decrease in turbidity was observed at 25° C. and 35° C., which might have been caused by an increase in particle size of possible precipitated aggregates.

Figure 12:
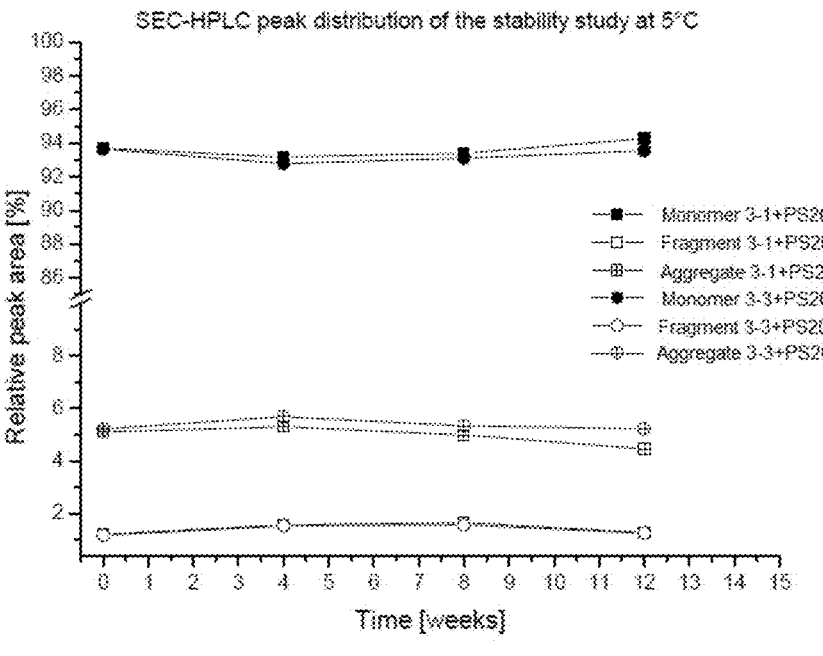
Figure 13:
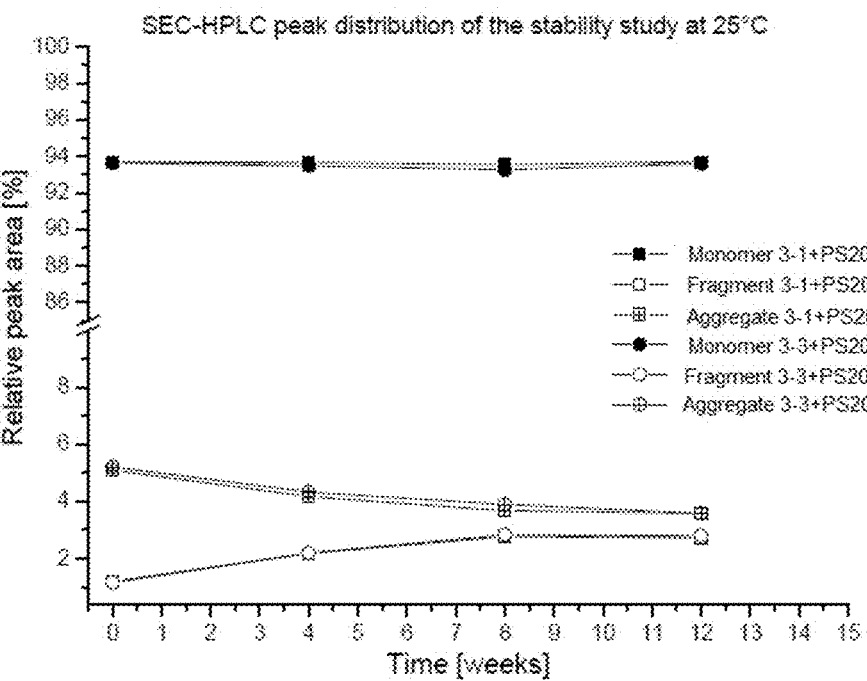
Figures 14, 15:
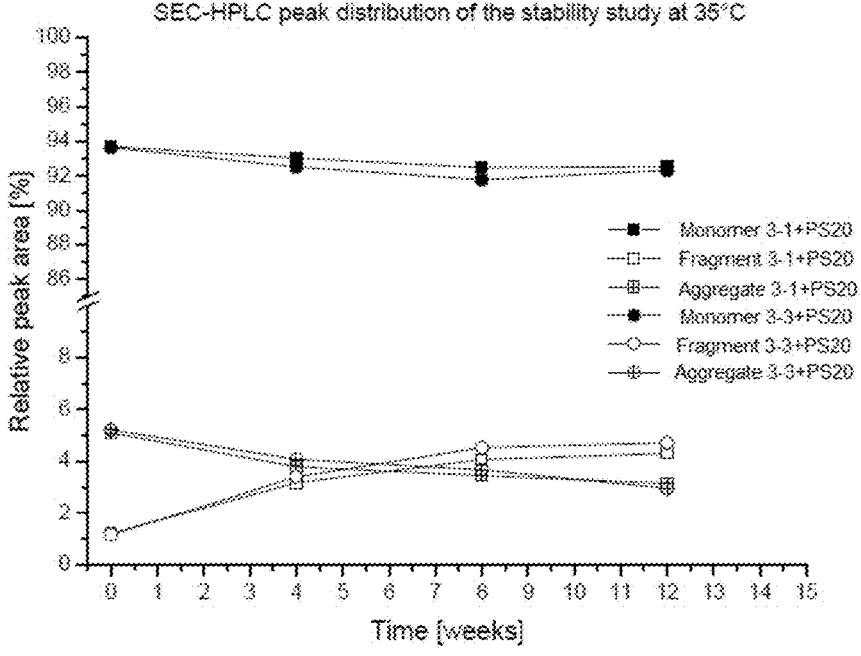

FIGS. 12-14 shows the monomer, aggregate and fragment content of the formulation variants during the stability study. The SE-HPLC analyses revealed that at 5° C.±3° C. and at 25° C. the relative monomer content remained nearly constant. A slight decrease in relative monomer peak area was observed for both formulation variants at 35° C. The aggregate content remained constant at a storage temperature of 5° C.±3° C. In contrast, the aggregate content dropped during the stability study at 25° C. and 35° C. This was most likely caused by the precipitation of formed aggregates at 25° C. and 35° C. that was in line with the increased turbidity of the samples. The fragment content increased at 25° C. and 35° C. whereas it remained nearly constant at 5° C.±3° C. in both formulations.

Capillary zone electrophoresis (CZE) was used to monitor the charge heterogeneity of the antibody and is a measure for chemical stability of the sample. FIG. 15 shows the charge heterogeneity of the formulation variants during the stability study. The charge heterogeneity of the samples remained nearly constant during the first 4 weeks of stability testing independent of the storage temperature. After 8 weeks, the main peak area decreased in all three storage temperatures for both formulation variants. Higher degradation was observed at elevated temperatures. After 12 weeks, the main peak area of both formulations remained unchanged at storage temperatures of 5° C.±3° C. and 25° C.

Figure 16:
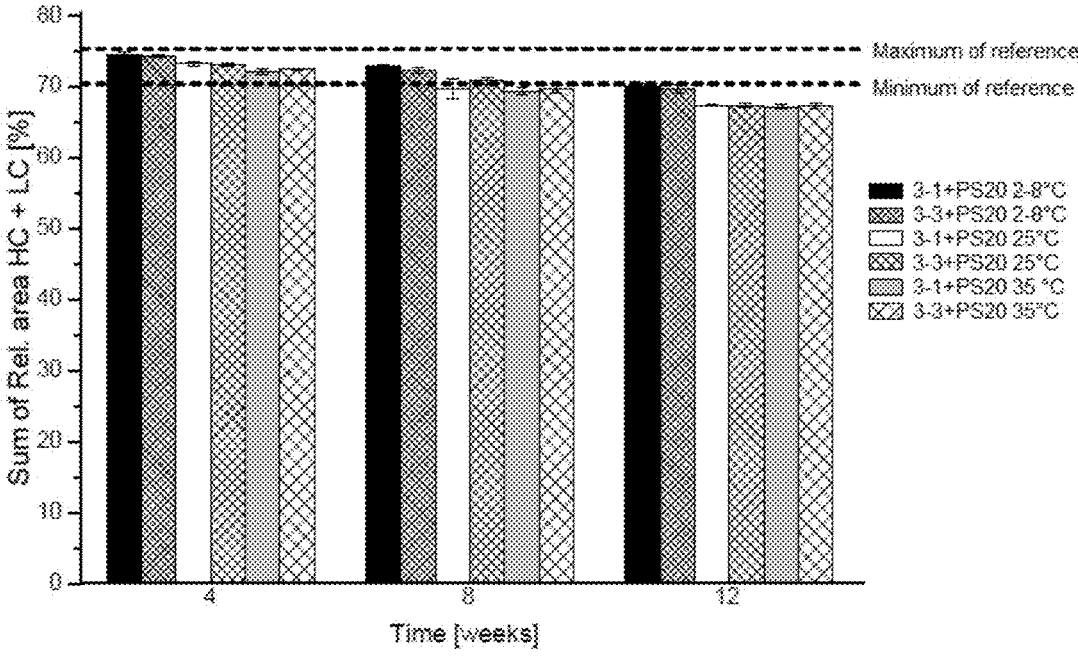

FIG. 16 shows the purity by reduced RP-HPLC of the formulation variants 3-1+PS20 and 3-3+PS20 during the stability study. The dashed lines in Figure display the minimum and maximum purity of the FP-1305 reference measured during the stability study (at each time point FP-1305 reference was analyzed at the beginning and at the end of each sequence). Reduced RP-HPLC detects mainly oxidized degradation products of antibodies. In the RP-HPLC analyses, both formulation variants 3-1+PS20 and 3-3+PS20 showed a slight increase in degradation products (oxidized forms) during stability testing at 25° C. and 35° C. Both formulation variants showed comparable chemical degradation. Chemical degradation was revealed to be the most critical degradation pathway of FP-1305 drug substance.

Based on the results, both formulations 3-1+PS20 and 3-3+PS20 provides a stable formulation for anti-CLEVER-1 antibody. According to a preferred embodiment of the present invention, a pH of formulation solution is adjusted to 6.0 and buffered with L-histidine. pH can be adjusted with a sufficient quantity (q.s.) of 6 N hydrochloric acid and, if needed, with 10 N sodium hydroxide. L-methionine is added to improve stability and acting as an antioxidant. Trehalose dihydrate or proline is also added to the formulation to improve the stability, acting as a stabilizer. Non-ionic polysorbate 20 is used as a surfactant to further stabilize the molecule in liquid formulation. Formulation 3-1+PS20 was slightly less turbid than formulation 3-3+PS20. Hence, according to a preferred embodiment of the present invention, a formulation comprises trehalose, such as trehalose dihydrate as a stabilizer. Formulations are stable at least at 2-8° C. (5° C.±3° C.).

Stability Test (18 months at 5° C.±3° C.)

The formulation 3-1+PS20 (the concentration of FP-1305 drug substance was 25 mg/mL) has stored in DIN 10R glass vials of hydrolytic class I for 18 months at 5° C.±3° C. A bromobutyl rubber stopper with FluroTec coating was chosen to minimize the interactions between the drug product and the closure and to maintain the container closure integrity.

After 18 months stored at 5° C.±3° C., no significant variation was noted for pH, osmolality, sub-visible particles (HIAC), concentration (UV), identity (image Capillary Isoelectric Focusing (icIEF)), or purity (SE-HPLC). Regarding the Appearance of the solution, the sample remains clear (comparable to water) unlike the previous time points (slightly opalescent solution. The results are shown in FIG. 18.

Potency Study

Figure 17:
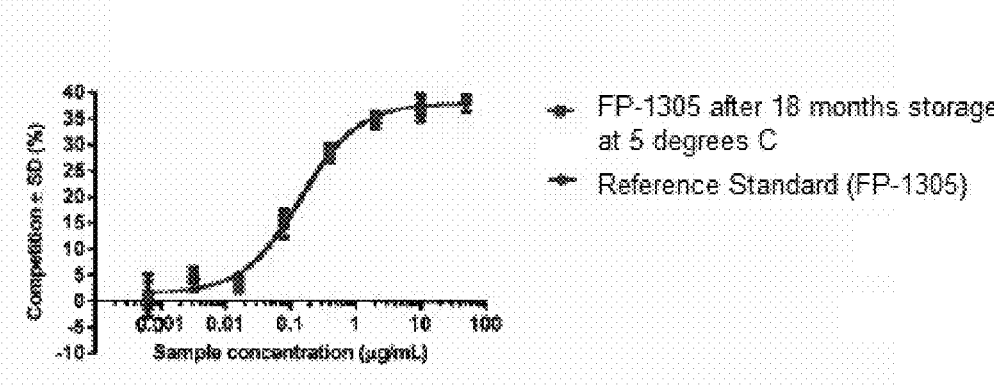

The formulation 3-1+PS20 (the concentration of FP-1305 drug substance was 25 mg/mL) has stored at 5° C.±3° C. and after 18-month storage biological activity assay to measure the potency of anti-CLEVER-1 antibody has been performed. A biological function is determined using cell-based assay. The antibody concentration necessary to achieve half-maximal effectivity is called $EC_{50}$. Potency of the test sample was assessed by comparing the curves of the test samples to a reference material by the ration of EC50's. Potency was expressed as percent relative potency of reference material (FP-1305 stored in −70° C.). The formulation according to the present invention exhibit biological activity for long periods of time, including up to at least about eighteen months. The result of the biological activity assay is presented in FIG. 17. Relative potency after storage period was 92.3%.

Clinical Study

Anti-CLEVER-1 antibody FP-1305 is currently being tested for safety and preliminary efficacy in a Phase I/II study in patient with advanced solid tumors (clinicaltrials.gov NCT03733990: A Study to Evaluate Safety, Tolerability and Preliminary Efficacy of FP-1305 in Cancer Patients (MATINS)). The accumulated safety information indicates a good tolerability for FP-1305. This is very positive indicator of product characteristics, as traditional cytotoxic anti-cancer treatments have been associated with dose dependent and treatment limiting toxicity. Tolerability and level of undesired side effects observed in human are also in line with the pre-clinical observations of inhibiting CLEVER-1 function in rodent and in monkey. First human data also suggest good clinical efficacy of 8/30 treated patients with very advanced metastatic tumors showed no progression in their target lesions, and 3 patients showed clear tumor shrinkage in follow-up (FIG. 19).

Figure 19:
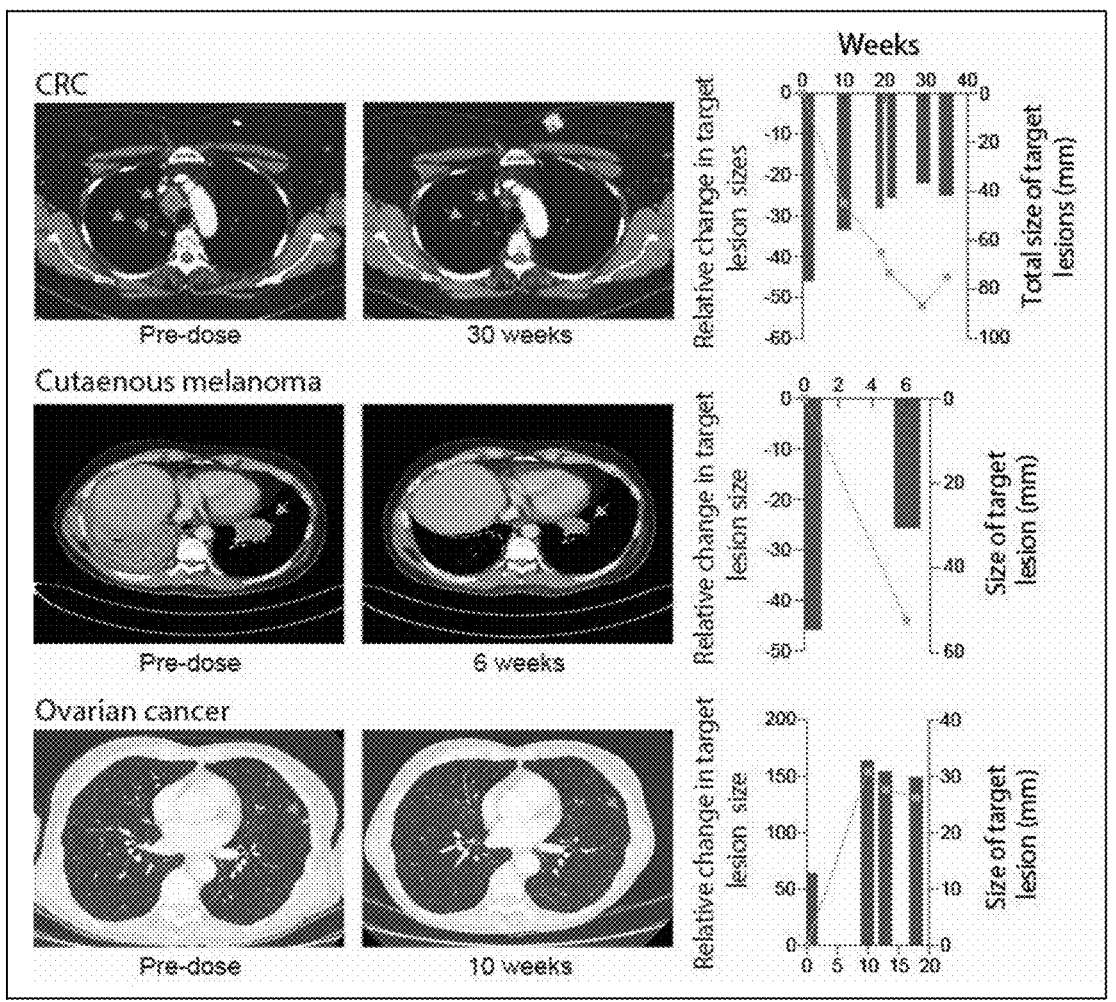
FIG. 19 shows baseline and follow up computed tomography scan images of the metastatic lesions in patients with best responses in a phase I/II clinal study.

FIG. 19 shows baseline and follow up computed tomography scan images of the metastatic lesions in patients with best responses. Arrows point shrinking lung metastases in patients with microsatellite stable (MSS) metastatic colorectal cancer (CRC), melanoma and ovarian cancer. Size of the target lesions and change over time are presented on the right side of each Figure.

In a Phase I/II study, it has also been observed that patient that receive anti-CLEVER-1 antibody FP-1305, an increase in plasma LDL (P-LDL) levels as shown in Table 6, indicating that LDL binding and uptake is inhibited or blocked by CLEVER-1 monocytes/macrophages. Anti-CLEVER-1 antibody FP-1305 prevents macrophage LDL cholesterol uptake and foam cells formation, since acLDL is not digested. This is seen as an increase in LDL levels of cancer patients treated with FP-1305.

First (pre-dose) fasting plasma sample taken prior to initiating FP-1305. Second fasting plasma sample (post-dose) taken at the end of the first 3 weeks treatment cycle of an anti-CLEVER-1 antibody FP-1305. The results are shown in Table 6, plasma LDL (P-LDL) levels expressed as mmol/L.

TABLE 6

| | P-LDL (mmol/L) | |
| | Pre-dose | Post dose |
| --- | --- | --- |
| Patient 1 | 2.7 | 3.4 |
| Patient 2 | 1.9 | 2.5 |
| Patient 3 | 3.3 | 3.5 |

TABLE 6-continued

| | P-LDL (mmol/L) | |
| | Pre-dose | Post dose |
| --- | --- | --- |
| Patient 4 | 3.8 | 4.8 |
| Patient 5 | 2.7 | 3.0 |

The invention claimed is:

1. A stable pharmaceutical formulation, which comprises
   1-100 mg/ml of an anti-CLEVER-1 antibody or antigen
      binding fragment(s) thereof,
   5-50 mM of a histidine buffer in combination with 150
      mM-400 mM of a trehalose as a stabilizing agent,
      wherein the pH of said pharmaceutical formulation is in
      the range of 5.5-6.5, and
   0.01-0.1% (w/v) of polysorbate as a non-ionic surfactant,
      wherein the anti-CLEVER-1 antibody or antigen binding
      fragment(s) thereof comprises the amino acid sequence
      SEQ ID NO: 7 of a heavy chain and the amino acid
      sequence SEQ ID NO: 8 of a light chain.

2. The formulation according to claim 1, wherein the
anti-CLEVER-1 antibody is bexmarilimab or bexmarilimab
variant or the antibody in a bexmarilimab biosimilar.

3. The formulation according to claim 1, wherein the
anti-CLEVER-1 antibody is antibody FP-1305 (DSM
ACC3361).

4. The formulation according to claim 1, wherein the
formulation comprises histidine buffer and has a pH between
5.8 and 6.2.

5. The formulation according to claim 1, wherein the
histidine buffer comprises L-histidine.

6. The formulation according to claim 1, wherein the
formulation comprises 5-20 mM or 5-15 mM of the histidine
buffer.

7. The formulation according to claim 1, wherein the
formulation comprises 200-360 mM of trehalose as a stabi-
lizing agent.

8. The formulation according to claim 1, wherein the
formulation comprises polysorbate 20 as a non-ionic sur-
factant.

9. The formulation according to claim 8, wherein the
formulation comprises 10-100 mg/ml of an anti-CLEVER-1
antibody or antigen binding fragment(s) thereof.

10. The formulation according to claim 1, wherein the
formulation comprises 0.01-0.05% (w/v) of polysorbate.

11. The formulation according to claim 1, wherein the
composition further comprises an antioxidant.

12. The formulation according to claim 1, wherein the
formulation comprises:
   (i) 1-100 mg/ml of an anti-CLEVER-1 antibody or anti-
      gen binding fragment(s) thereof,
   (ii) 5-50 mM of histidine buffer,
   (iii) 150-400 mM of trehalose as the stabilizing agent,
   (iv) 0.01-0.1% (w/v) of polysorbate as the non-ionic
      surfactant, and
   (v) 5-40 mM of L-methionine as the antioxidant,
   wherein the pH of said composition is between 5.5 and
      6.5.

13. The formulation according to claim 1, wherein the
formulation is a liquid formulation or in a lyophilized form.

14. The formulation according to claim 1, wherein the
formulation comprises 240-320 mM of trehalose as a stabi-
lizing agent.

15. The formulation according to claim 1, wherein the
formulation comprises 270-290 mM of trehalose as a stabi-
lizing agent.

16. The formulation according to claim 10, wherein the
formulation comprises 0.01-0.05% (w/v) of polysorbate 20.

17. The formulation according to claim 11, wherein the
antioxidant comprises L-methionine.

18. The formulation according to claim 17, wherein the
composition comprises 5-40 mM of L-methionine.

19. The formulation according to claim 17, wherein the
composition comprises 15-25 mM of L-methionine.

* * * * *